(12) United States Patent
Shimoboji

(10) Patent No.: US 7,456,275 B2
(45) Date of Patent: Nov. 25, 2008

(54) HYALURONIC ACID MODIFICATION PRODUCT

(75) Inventor: Tsuyoshi Shimoboji, Gotenba (JP)

(73) Assignee: Chugai Seiyaku Kabushiki Kaisya, Tokyo (JP)

( * ) Notice: Subject to any disclaimer, the term of this patent is extended or adjusted under 35 U.S.C. 154(b) by 396 days.

(21) Appl. No.: 10/511,707

(22) PCT Filed: Apr. 18, 2003

(86) PCT No.: PCT/JP03/04949

§ 371 (c)(1), (2), (4) Date: Oct. 15, 2004

(87) PCT Pub. No.: WO03/087019

PCT Pub. Date: Oct. 23, 2003

(65) Prior Publication Data

US 2005/0164980 A1 Jul. 28, 2005

(30) Foreign Application Priority Data

| Apr. 18, 2002 | (JP) | ................................ 2002-116508 |
| Jul. 18, 2002 | (JP) | ................................ 2002-209429 |
| Nov. 15, 2002 | (JP) | ................................ 2002-331551 |

(51) Int. Cl.
*A61K 31/728* (2006.01)
*C07H 5/06* (2006.01)
*C08B 37/08* (2006.01)

(52) U.S. Cl. ......................... 536/55.1; 514/54

(58) Field of Classification Search ................ 514/54; 536/55.1
See application file for complete search history.

(56) References Cited

U.S. PATENT DOCUMENTS

| 5,470,911 A | * | 11/1995 | Rhee et al. ................. 525/54.1 |
| 5,490,978 A | * | 2/1996 | Spaltro et al. ................. 424/49 |
| 2007/0031503 A1 | * | 2/2007 | Hirakura et al. ............. 424/490 |

FOREIGN PATENT DOCUMENTS

| JP | 04-261664 | 9/1992 |
| JP | 05-262882 | 10/1993 |
| JP | 09-227329 | 9/1997 |
| JP | 11-169703 | 6/1999 |
| JP | 2002-256075 | 9/2002 |
| WO | WO-95/15152 A1 | 6/1995 |
| WO | WO-97/24430 A1 | 7/1997 |
| WO | WO-99/18142 A1 | 4/1999 |
| WO | WO-00/27405 A1 | 5/2000 |

OTHER PUBLICATIONS

"Soshiki Kogaku ni Okeru Jinko Saibo-gai Matrix Sekkai: Kan'onsei Hyaluronic Acid no Gosei to Kozoka' (Artificial Extracellular Matrix Design in Tissue Engineering: Synthesis of Thermoresponsive Hyaluronic Acid and Its Supramolecular Organization)" by Oya et al., The Japanese Journal of Artificial Organs (2000), 29(2), pp. 446-451.

Patent Abstracts of Japan for JP2002-256075 published on Sep. 11, 2002.

Patent Abstracts of Japan for JP04-261664 published on Sep. 17, 1992.

"Injectable Hyaluronic Acid Gel for Soft Tissue Augmentation—A Clinical and Histological Study" by Duranti et al., American Society for Dermatologic Surgery, Inc., 1998, pp. 1317-1325.

Patent Abstracts of Japan for JP05-262882 published on Oct. 12, 1993.

Patent Abstract of Japan for JP09-227329 published on Sep. 2, 1997.

Patent Abstracts of Japan for JP11-169703 published on Jun. 29, 1999.

"Temperature-responsive gels and thermogelling polymer matrices for protein and peptide delivery" by Bromberg et al., Advanced Drug Delivery Reviews 31, 1998, pp. 197-221.

"A Retention Test after Single Intra-articular Administration of High Molecular Weight Sodium Hyaluronate (NRD101) into the Rabbit Knee" by Umeda et al., Japan Pharmacology Therapeutics, vol. 22, Supplement, Mar. 1994, pp. 387(S-779)-393(S-785).

"Thermoresponsive Artificial Extracellular Matrix for Tissue Engineering: Hyaluronic Acid Bioconjugated with Poly(N-isopropylacrylamide) Grafts" by Ohya et al., Biomacromolecules 2001, 2, pp. 856-863.

"Temperature-responsive and degradable hyaluronic acid/Pluronic composite hydrogels for controlled release of human growth hormone" by Kim et al., Journal of Controlled Release 80 (2002) pp. 69-77.

* cited by examiner

*Primary Examiner*—Shaojia Anna Jiang
*Assistant Examiner*—Eric S Olson
(74) *Attorney, Agent, or Firm*—Darby & Darby P.C.

(57) ABSTRACT

The present invention provides a safe hyaluronic acid base material that is suitable for use in practical hyaluronic acid pharmaceutical preparations capable of distribution at room temperature and having such a low viscosity that injection is easy. The hyaluronic acid pharmaceutical preparations can reside in a joint cavity for a prolonged period of time while exhibiting analgesic effects. More speclfically, there is provide a hyaluronic acid modification product in which hyaluronic acid and/or a pharmaceutically acceptable salt thereof is bounded to a block polymer selected from PEO-PPO-PEO, PPO-PEO-PPO, PEO-PLGA-PEO, PLGA-PEO-PLGA, PEO-PLA-PEO and PLA-PEO-PLA. The hyaluronic acid modification product, despite capability of distribution at room temperature and ease in handling because of the low viscosity, can have its viscoelasticity rapidly increased after injection into a living body, so that it is highly useful in treatment of joint diseases, aid in surgical operation, repair of tissue, etc. as a main ingredient of novel and practical hyaluronic acid pharmaceutical preparations.

14 Claims, 14 Drawing Sheets

HYALURONIC ACID MODIFICATION PRODUCT

CROSS-REFERENCE TO PRIOR APPLICATION

This is a U.S. national phase application under 35 U.S.C. §371 of International Patent Application No. PCT/JP03/04949 filed Apr. 18, 2003, and claims the benefit of Japanese Patent Application Nos. 2002-116508 filed Apr. 18, 2002; 2002-209429 filed Jul. 18, 2002 and 2002-331551 filed Nov. 15, 2002 which are incorporated by reference herein. The International Application was published in Japanese on Oct. 23, 2003 as WO 03/087019 A1 under PCT Article 21(2).

TECHNICAL FIELD OF THE INVENTION

The present invention relates to a novel hyaluronic acid modification product; a pharmaceutical preparation for treating joint diseases comprising the hyaluronic acid modification product as its main component; and a method of treating joint diseases using the hyaluronic acid modification product. The present invention also relates to an assisting or treating agent for surgical operation comprising the hyaluronic acid modification product as its main component; and a method of surgical operation using the assisting or treating agent. Further, the present invention relates to a tissue repairing agent comprising the hyaluronic acid modification product as its main component; and a tissue repairing method using the tissue repairing agent.

BACKGROUND OF THE INVENTION

A number of methods for treating joint diseases, such as loss of articular cartilage, rheumatoid arthritis, osteoarthritis or scapulo-humeral periarthritis, have been proposed for the recent 40 years. Although a method of articular cartilage regeneration by autologous cell transplantation is also attempted at present, this method requires several surgical operations, lacks simplicity and imposes great burden on patients. In cases where artificial joints are used, problems of bio-compatibility, durability, and the like arise. A method of treating joint diseases with a drug that dissolves these problems has been desired for long.

Under circumstances, a treating method in which hyaluronic acid is directly injected into the joint cavity is widely used in the field of medical treatment [e.g. Artz (product name) manufactured by Seikagaku Corporation and sold by Kaken Pharmaceutical is used]. Hyaluronic acid is one of the main components of synovial fluid and produces analgesic effect in joints due to its viscoelastic effect and anti-inflammatory effect. Generally, in the synovial fluid of patients with arthritis such as osteoarthritis, rheumatoid arthritis, etc., it is known that the concentration and molecular weight of hyaluronic acid are lower than the concentration and molecular weight in normal synovial fluid. This is considered to be associated with the occurrence of painful conditions attributable to the decreasing of the lubricant effect and shock-absorbing effect of the synovial fluid. However, the clearance of hyaluronic acid in the joint cavity is quick. Although use of high molecular weight (about 1,900,000 daltons) hyaluronic acid [Suvenyl (product name) manufactured by Aventis Pharma Japan and sold by Chugai Pharmaceutical] has been tried to prolong the residence time, low temperature flow is necessary because of its high molecular weight and injection pressure tends to be high because of its high viscosity. The residence time of this hyaluronic acid in the joint cavity is about five days (Japanese Pharmacology and Therapeutics, 22 (S-3), S779 (1994)), and the duration of analgesic effect is about one week. Further sustaining of the effect is also demanded for the purpose of improving compliance in patients.

On the other hand, another trial to prolong the residence time has been made by partially cross-linking hyaluronic acid chemically [for example, Synvisk (product name) from Genzyme Biosurgery (Japanese Unexamined Patent Publication No. 4-261664 (U.S. Pat. No. 5,399,351; EP Patent No. 466300)); and Restylane (product name) from Q-Med (Dermatologic Surgery, 24, 1317-1325, 1998)]. However, problems such as induction of inflammation by the cross-linking agent are apprehended. A gel material utilizing physical cross-linking by hydrogen bonds or the like between hyaluronic acid molecules has also been reported (International Patent Publication Number WO00/27405). However, the bridge begins to collapse when the gel material is dissolved in water. Therefore, it is difficult to distribute this material as an easy-to-handle liquid preparation (i.e. injection) like the currently used hyaluronic acid preparations.

On the other hand, poly-N-substituted acrylamide derivatives, poly-N-substituted methacrylamide derivatives, polyvinyl methyl ethers, polyvinyl alcohol partial oxide, etc. are known as thermo-responsive polymers. As a thermo-responsive polymer highly safe in the living body, a polyethylene oxide-polypropylene oxide-polyethylene oxide block polymer (PEO-PPO-PEO; product name: Pluronic) is known, and was approved by the US Food and Drug Administration (FDA) (approval grades: F68 and F127). As a similar polymer, a polypropylene oxide-polyethylene oxide-polypropylene oxide block polymer (PPO-PEO-PPO; product name: Pluronic R) is known. It is reported that, when these polymers are used alone, it is possible to increase their viscosity and to turn them into gel by increasing the temperature (Adv. Drug. Delivery Rev., 31, 197-221 (1998)). However, in order to achieve such increased viscosity or gelation, it is necessary to use them at a high concentration of 16% w/v or more, which is disadvantageous in terms of safety and drug carrying ratio.

A polyethylene oxide-polylactic acid/polyglycolic acid copolymer-polyethylene oxide block polymer (PEO-PLGA-PEO; product name: Regel) or a polylactic acid/polyglycolic acid copolymer-polyethylene oxide-polylactic acid/polyglycolic acid copolymer block polymer (PLGA-PEO-PLGA; product name: Regel) each of which has a polylactic acid/polyglycolic acid copolymer instead of PPO in its hydrophobic portion; or a polyethylene oxide-polylactic acid-polyethylene oxide block polymer (PEO-PLA-PEO) or a polylactic acid-polyethylene oxide-polylactic acid block polymer (PLA-PEO-PLA) each of which has a polylactic acid polymer instead of PPO in its hydrophobic portion is known to have a thermo-responsive function similar to the thermal responsiveness as described above (International Patent Publication Number WO99/18142).

Although common thermo-reversible hydrogel materials composed of such a thermo-responsive polymer and a hydrophilic polymer have been reported (Japanese Unexamined Patent Publications No. 5-262882, No. 9-227329, No. 11-169703; International Patent Publication Number WO95/15152), no example in which hyaluronic acid is combined with PEO-PPO-PEO, PPO-PEO-PPO, PEO-PLGA-PEO, PLGA-PEO-PLGA, PEO-PLA-PEO or PLA-PEO-PLA has been reported to date. Besides, such hydrogel materials are for use in external preparations or perfumes/cosmetics, and are not intended to be injected into the living body (e.g. into the joint cavity). A thermo-responsive polymer in which PEO-PPO-PEO is grafted on polyacrylic acid (International Patent Publication Number WO97/24430 (U.S. Pat. No.

5,709,815)) and a polymer in which poly-N-isopropyl acrylamide is grafted on hyaluronic acid (Biomacromol., 2, 856-863 (2001)) have also been reported. However, polyacrylic acid and poly-N-isopropyl acrylamide have safety problems such as the remaining of mutagenic monomers. Although a material in which hyaluronic acid is bound to Pluronic (Journal of Controlled Release, Vol. 80, Issue 1-3, pp. 69-77 (Apr. 23, 2002)) has also been reported, pharmaceutical use of the material itself is neither disclosed nor suggested. Besides, since the molecular weight of the material described in this document is 12,600, it is hard to be discharged from the living body and thus is not suitable for pharmaceutical use.

As described above, at present, there is no safe hyaluronic acid base material which is appropriate for use in practical hyaluronic acid preparations that are capable of distribution at room temperature, have a low viscosity allowing easy injection, and yet reside in the joint cavity for a long period of time to show analgesic effect.

Although use of hyaluronic acid preparations as an assisting agent for ophthalmic surgery (product name: Healon) or as a tissue repairing agent is also known, no assisting agent or treating agent for surgical operation has been known yet which is capable of distribution at room temperature, has a low viscosity allowing easy injection, and has an appropriate viscosity during operation.

SUMMARY OF THE INVENTION

As a result of extensive and intensive researches toward the solution of the above-described problems, the present inventors have found that the above problems can be dissolved by binding to hyaluronic acid and/or a pharmaceutically acceptable salt thereof a block polymer selected from polyethylene oxide-polypropylene oxide-polyethylene oxide block polymer, polypropylene oxide-polyethylene oxide-polypropylene oxide block polymer, polyethylene oxide-polylactic acid/polyglycolic acid copolymer-polyethylene oxide block polymer, polylactic acid/polyglycolic acid copolymer-polyethylene oxide-polylactic acid/polyglycolic acid copolymer block polymer, polyethylene oxide-polylactic acid-polyethylene oxide block polymer and polylactic acid-polyethylene oxide-polylactic acid block polymer. Thus, the present invention was completed based on this finding.

The present invention relates to a hyaluronic acid modification product in which hyaluronic acid and/or a pharmaceutically acceptable salt thereof is bound to a block polymer selected from polyethylene oxide-polypropylene oxide-polyethylene oxide block polymer, polypropylene oxide-polyethylene oxide-polypropylene oxide block polymer, polyethylene oxide-polylactic acid/polyglycolic acid copolymer-polyethylene oxide block polymer, polylactic acid/polyglycolic acid copolymer-polyethylene oxide-polylactic acid/polyglycolic acid copolymer block polymer, polyethylene oxide-polylactic acid-polyethylene oxide block polymer and polylactic acid-polyethylene oxide-polylactic acid block polymer.

The present invention also relates to the above-described hyaluronic acid modification product in which the block polymer is a polyethylene oxide-polypropylene oxide-polyethylene oxide block polymer or a polypropylene oxide-polyethylene oxide-polypropylene oxide block polymer.

The present invention also relates to the above-described hyaluronic acid modification product in which the most part of the block polymer is bound to the hyaluronic acid and/or a pharmaceutically acceptable salt thereof at only one of its two ends.

The present invention also relates to the above-described hyaluronic acid modification product in which the block polymer is bound to the hyaluronic acid and/or a pharmaceutically acceptable salt thereof at only one of its two ends.

The present invention also relates to the above-described hyaluronic acid modification product in which the block polymer is bound to the carboxyl group of the hyaluronic acid and/or a pharmaceutically acceptable salt thereof.

The present invention also relates to the above-described hyaluronic acid modification product, wherein the phase transition temperature of the hyaluronic acid modification product in physiological saline and/or phosphate physiological saline is in the range from 20° C. to 35° C. when the concentration of the hyaluronic acid modification product is 10.0% w/v or less.

The present invention also relates to the above-described hyaluronic acid modification product in which the weight average molecular weight of the block polymer is 1200 daltons or more.

The present invention also relates to the above-described hyaluronic acid modification product, wherein the ratio of introduction of the block polymer into the hyaluronic acid and/or a pharmaceutically acceptable salt thereof is 8 mol % or more per the glucuronic acid in the hyaluronic acid and/or a pharmaceutically acceptable salt thereof.

The present invention also relates to the above-described hyaluronic acid modification product, wherein the weight average molecular weight of the hyaluronic acid and/or a pharmaceutically acceptable salt thereof is 1,500,000 daltons or less.

Further, the present invention relates to a pharmaceutical composition comprising a hyaluronic acid modification product.

The present invention also relates to a pharmaceutical preparation for treating joint diseases, comprising the above-described hyaluronic acid modification product as its main component.

The present invention also relates to the pharmaceutical preparation for treating joint diseases, wherein the joint disease is loss of articular cartilage, rheumatoid arthritis, osteoarthritis or scapulo-humeral periarthritis.

The present invention also relates to the pharmaceutical preparation for treating joint diseases, comprising the above-described hyaluronic acid modification product as its main component, wherein the preparation is an injection.

The present invention also relates to a method of treating joint diseases, comprising administering to a patient an effective amount of the above-described hyaluronic acid modification product.

Further, the present invention relates to the method of treating joint diseases, comprising administering to a patient an effective amount of the above-described hyaluronic acid modification product, wherein the joint disease is loss of articular cartilage, rheumatoid arthritis, osteoarthritis or scapulo-humeral periarthritis.

Further, the present invention relates to an assisting or treating agent for surgical operation, comprising the above-described hyaluronic acid modification product as its main component.

The present invention also relates to the assisting or treating agent for surgical operation, comprising the above-described hyaluronic acid modification product as its main component, wherein the surgical operation is ophthalmic surgery or endoscopic mucosal resection.

The present invention also relates to a method of surgical operation, comprising applying to a target site a necessary amount of the above-described hyaluronic acid modification product.

The present invention also relates to the method of surgical operation, comprising applying to a target site a necessary amount of the above-described hyaluronic acid modification product, wherein the surgical operation is ophthalmic surgery or endoscopic mucosal resection.

Further, the present invention relates to a tissue repairing agent comprising the above-described hyaluronic acid modification product as its main component.

The present invention also relates to the tissue repairing agent comprising the above-described hyaluronic acid modification product as its main component, which is used for repairing damage to soft tissue, atrophic irregularity after surgical operation, damage caused by Mohs' chemosurgical treatment, wrinkles or laceration scars in wrinkles.

Further, the present invention relates to a tissue repairing method comprising applying to a target site a necessary amount of the above-described hyaluronic acid modification product.

The present invention also relates to the tissue repairing method comprising applying to a target site a necessary amount of the above-described hyaluronic acid modification product, which is a method for repairing damage to soft tissue, atrophic irregularity after surgical operation, damage caused by Mohs' chemosurgical treatment, wrinkles or laceration scars in wrinkles.

BEST MODES FOR CARRYING OUT THE INVENTION

Figure 1:
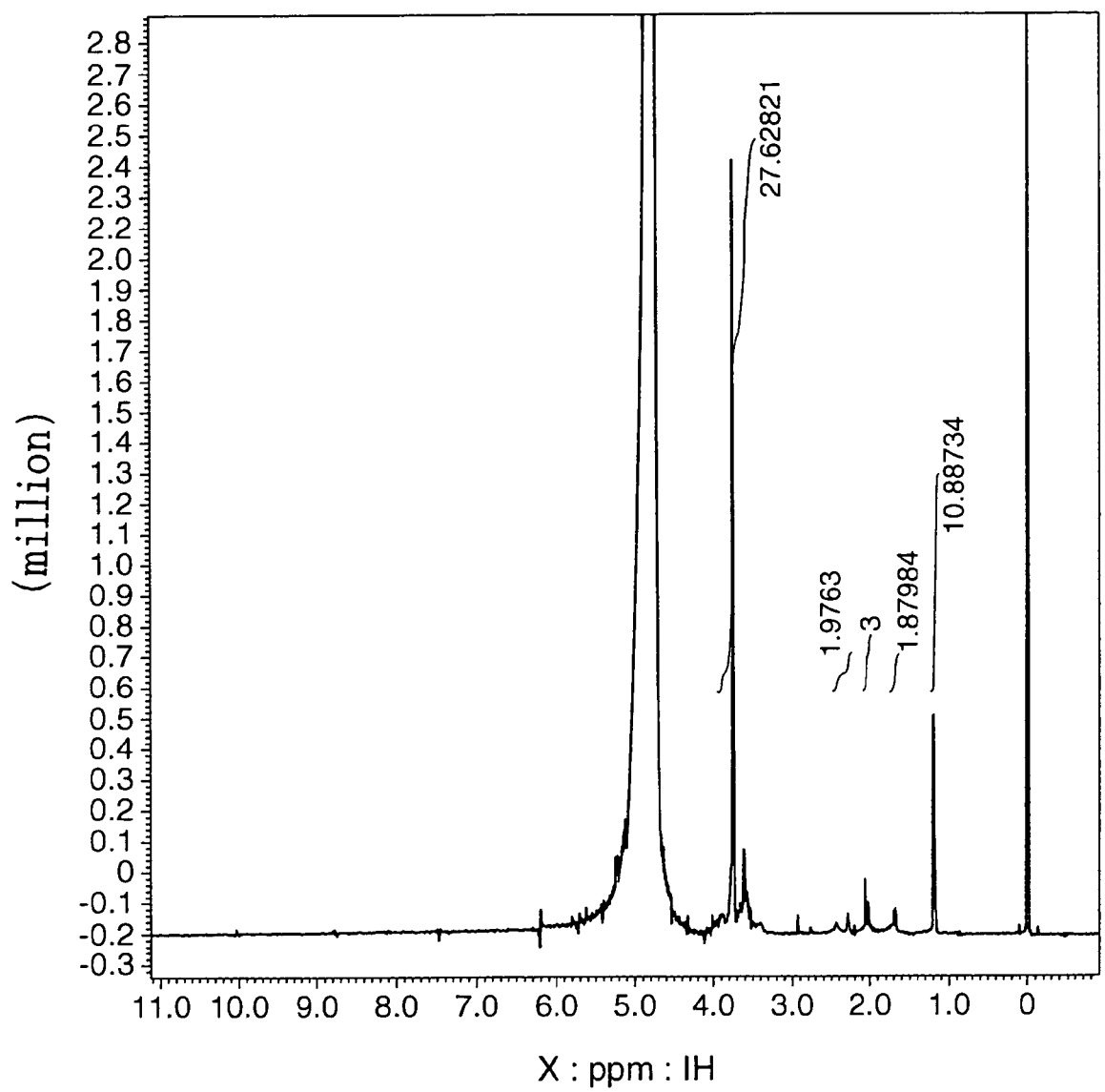
FIG. 1 is the proton NMR chart of the hyaluronic acid modification product of the invention obtained in Example 1-1.
Figure 2:
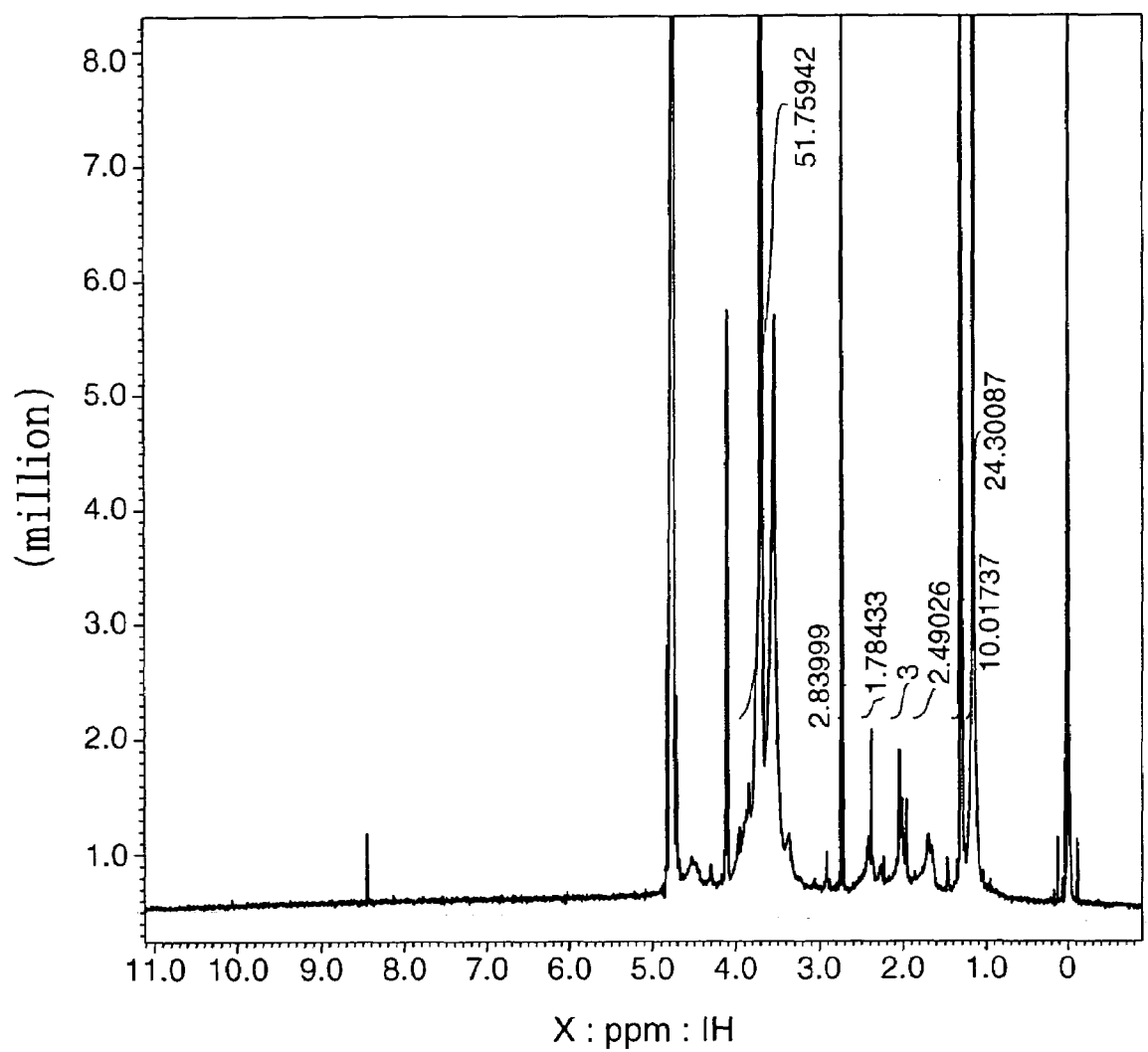
FIG. 2 is the proton NMR chart of the hyaluronic acid modification product of the invention obtained in Example 1-2.
Figure 3:
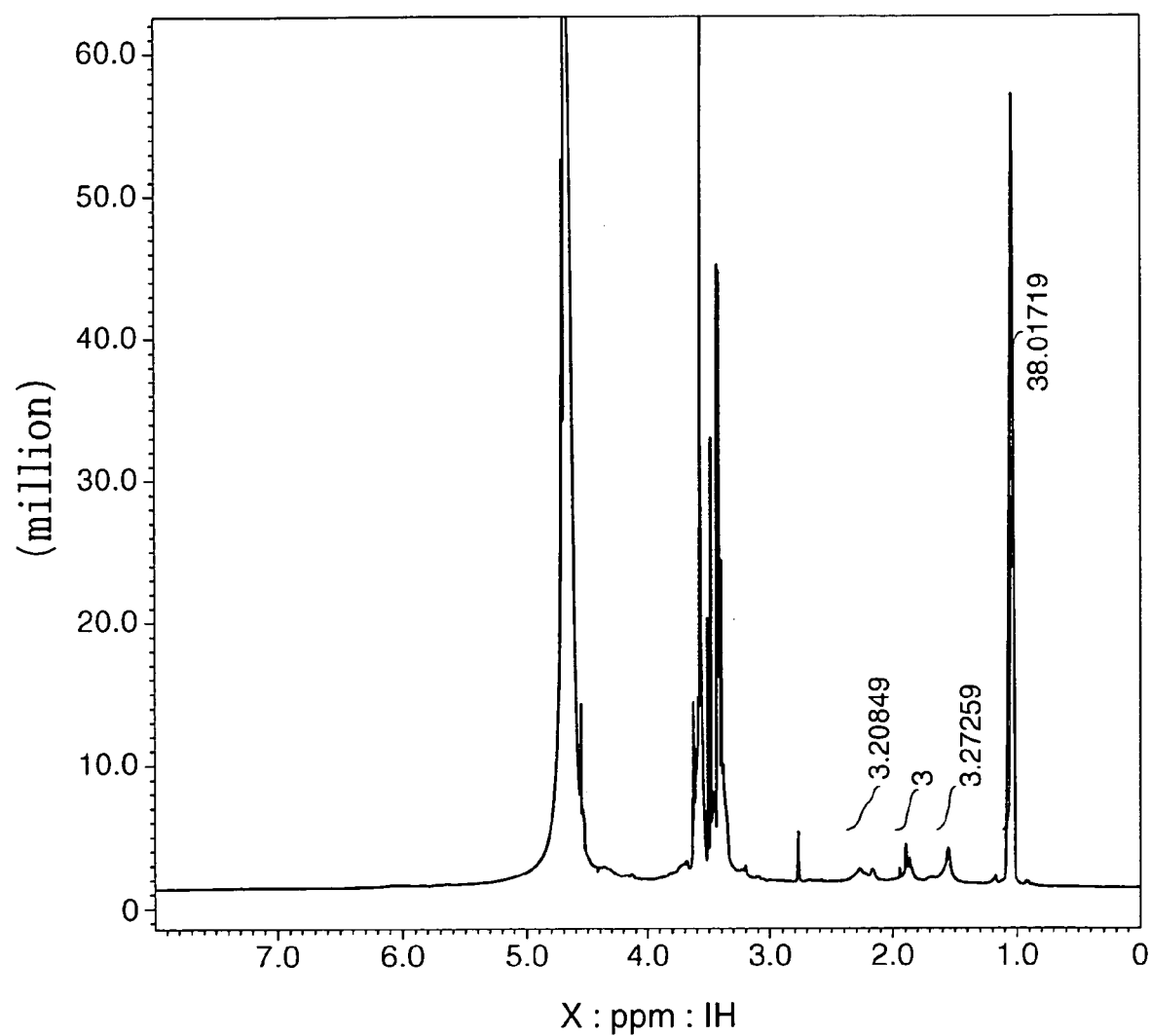
FIG. 3 is the proton NMR chart of the hyaluronic acid modification product of the invention obtained in Example 2-1.
Figure 4:
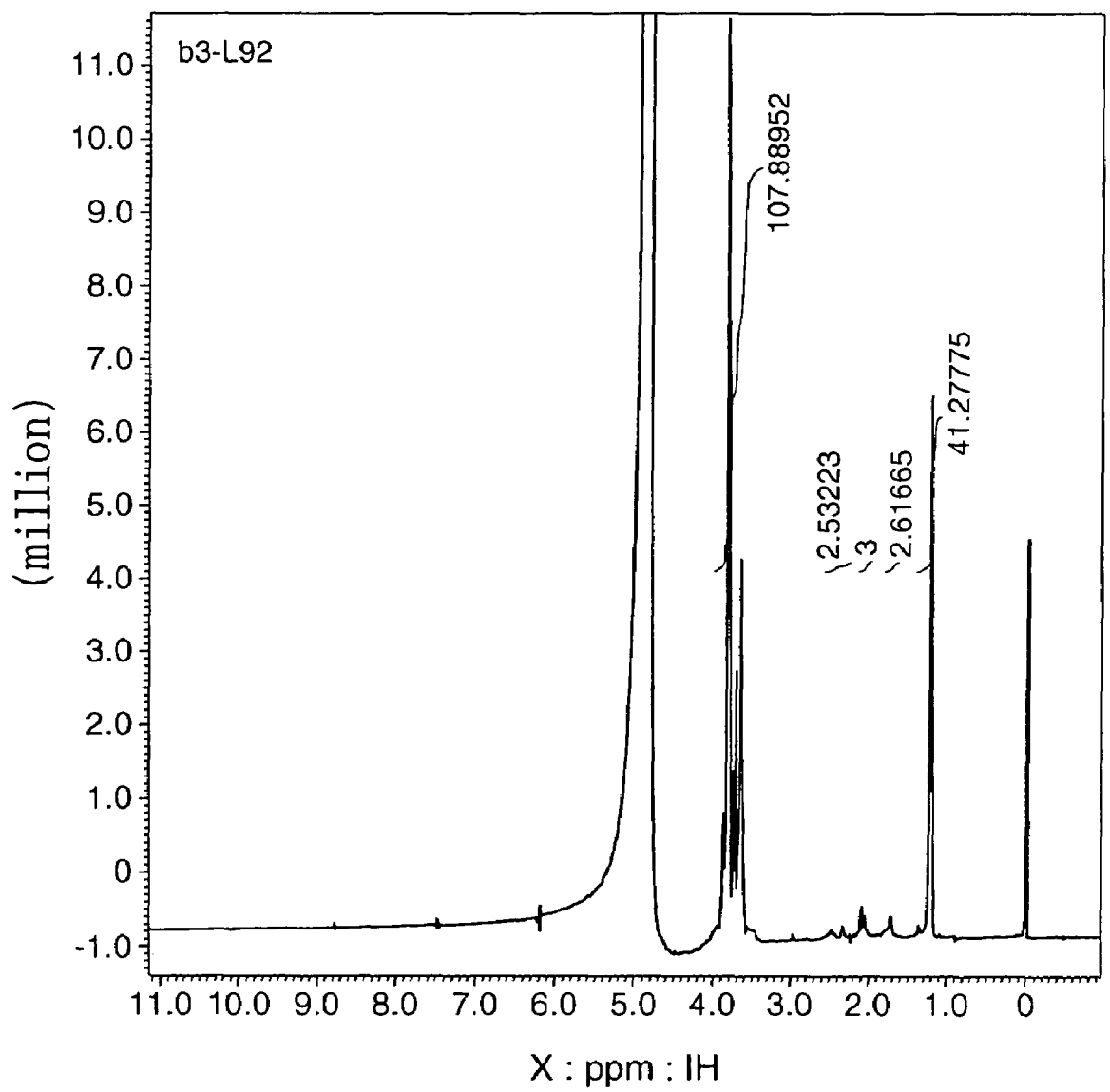
FIG. 4 is the proton NMR chart of the hyaluronic acid modification product of the invention obtained in Example 2-2.
Figure 5:
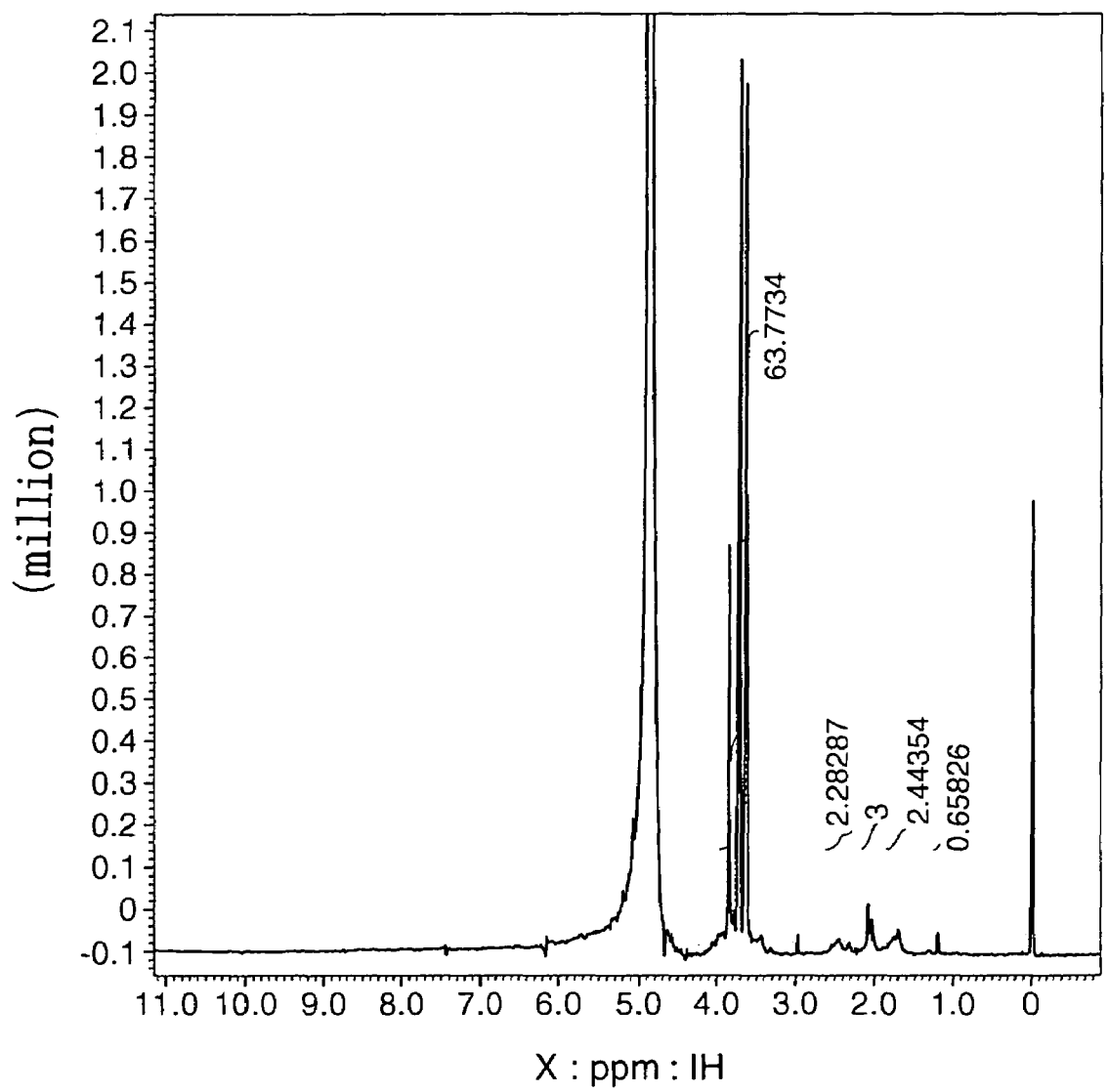
FIG. 5 is the proton NMR chart of the hyaluronic acid modification product obtained in Comparative Example 1.
Figure 6:
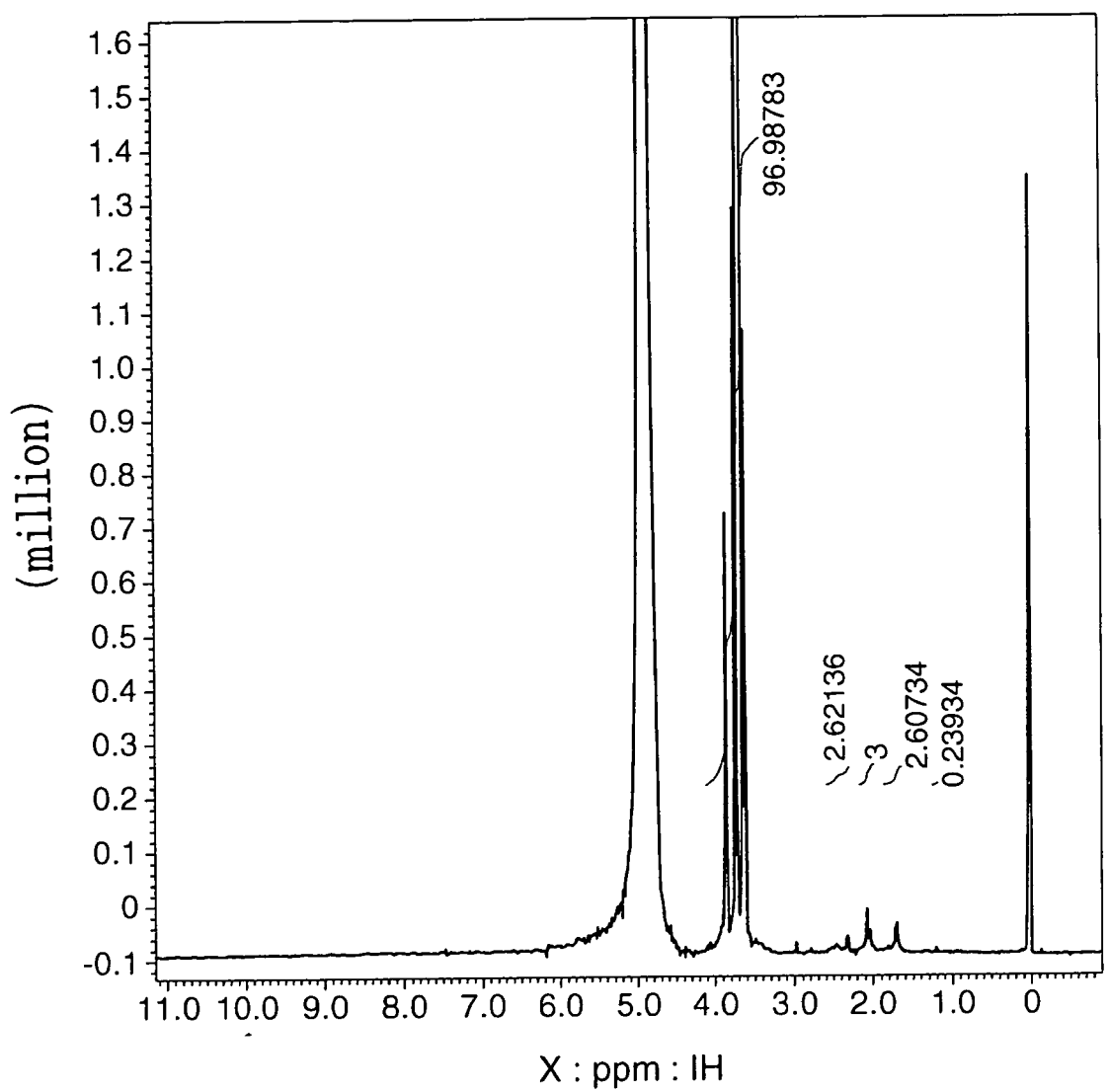
FIG. 6 is the proton NMR chart of the hyaluronic acid modification product obtained in Comparative Example 2.
Figure 7:
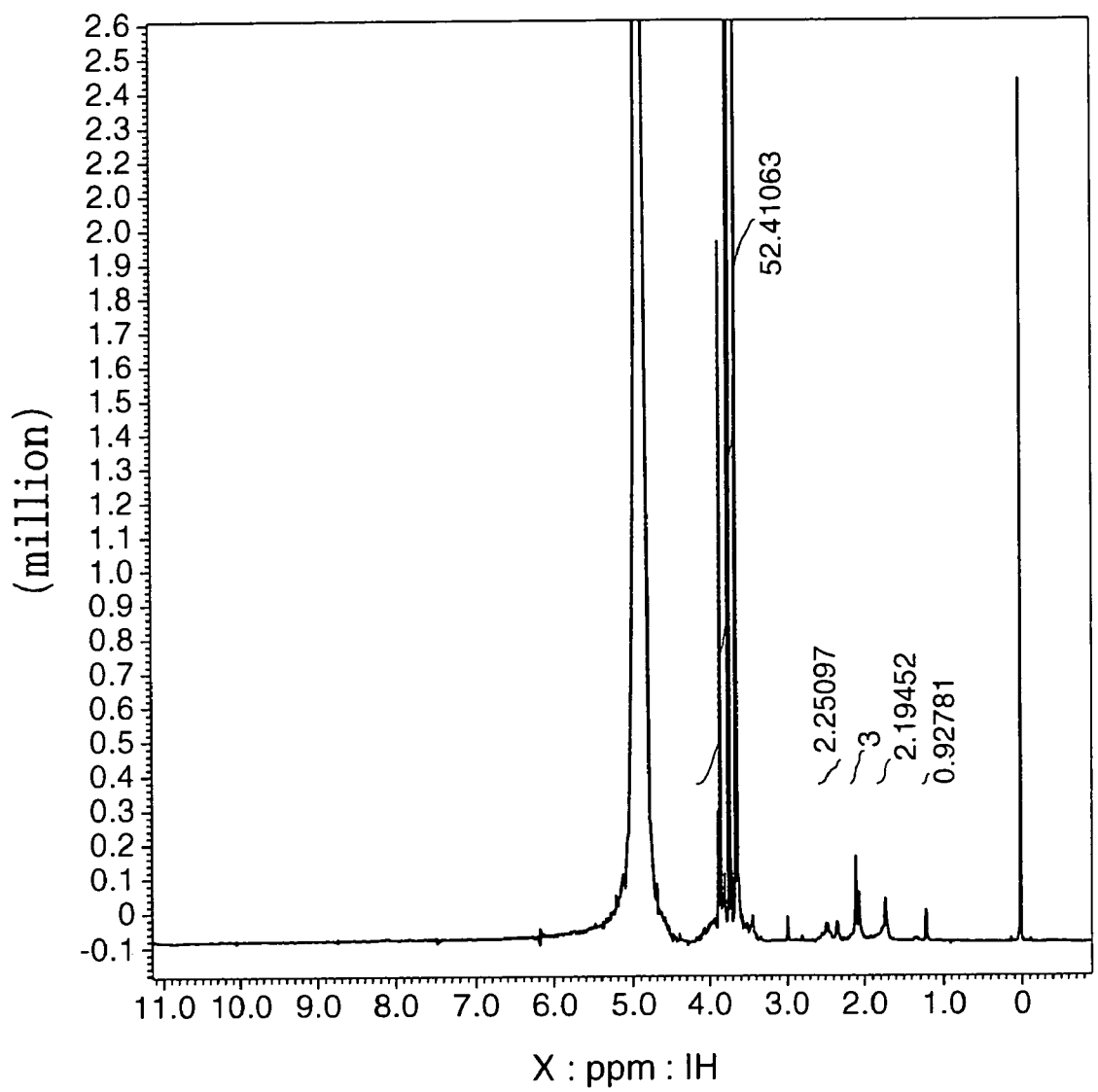
FIG. 7 is the proton NMR chart of the hyaluronic acid modification product obtained in Comparative Example 3.
Figure 8:
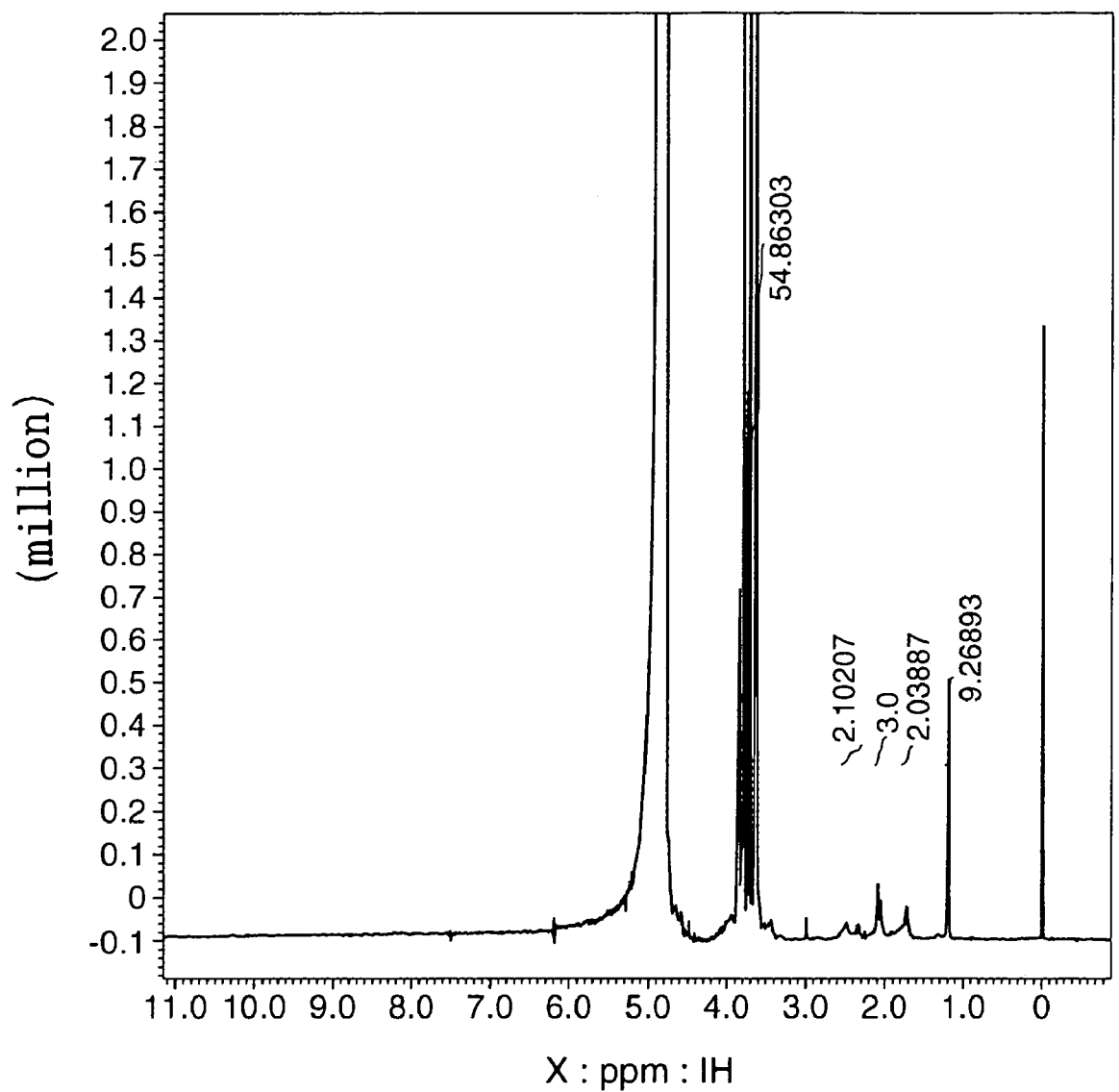
FIG. 8 is the proton NMR chart of the hyaluronic acid modification product obtained in Comparative Example 4.
Figure 9:
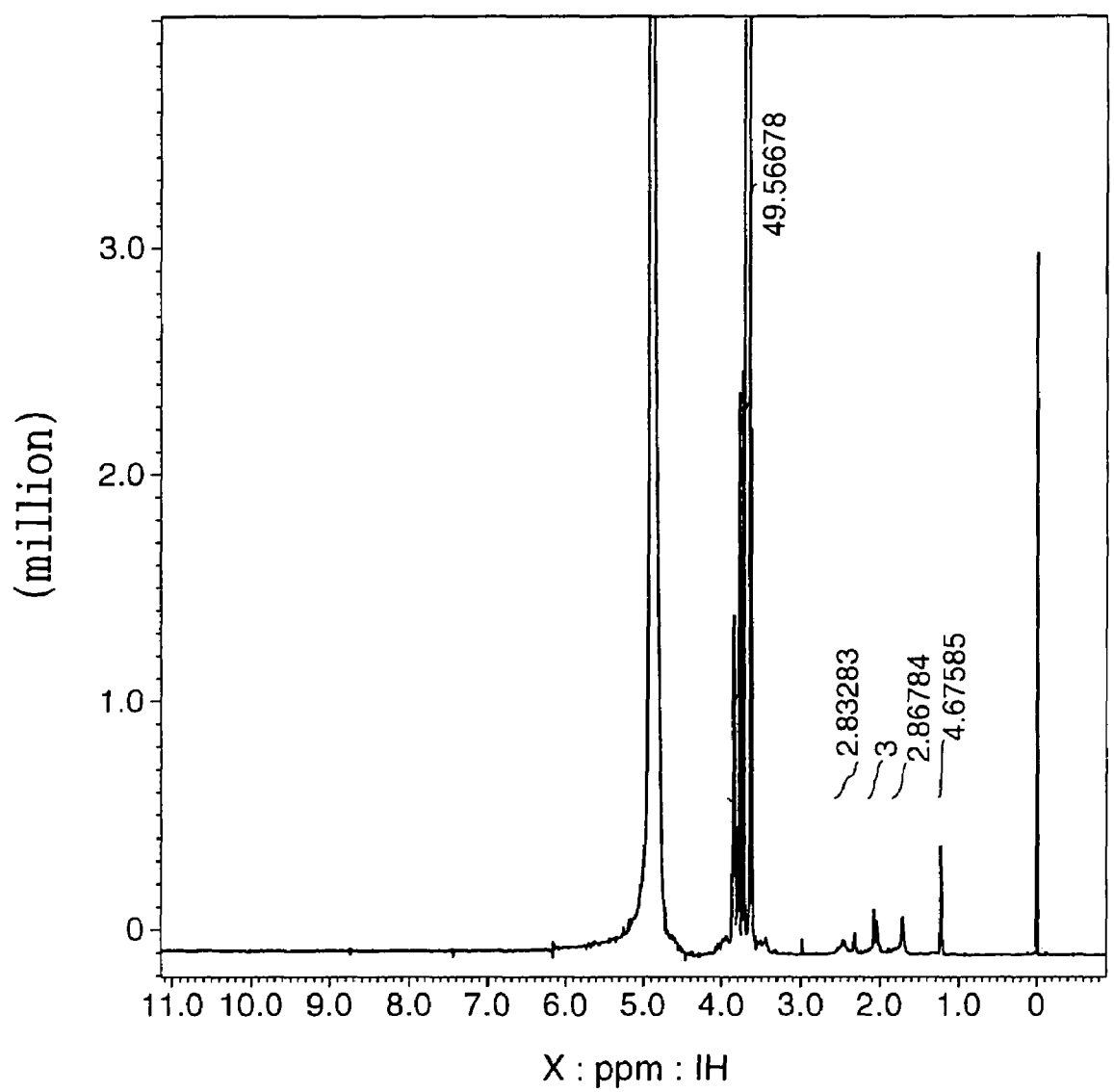
FIG. 9 is the proton NMR chart of the hyaluronic acid modification product obtained in Comparative Example 5.
Figure 10:
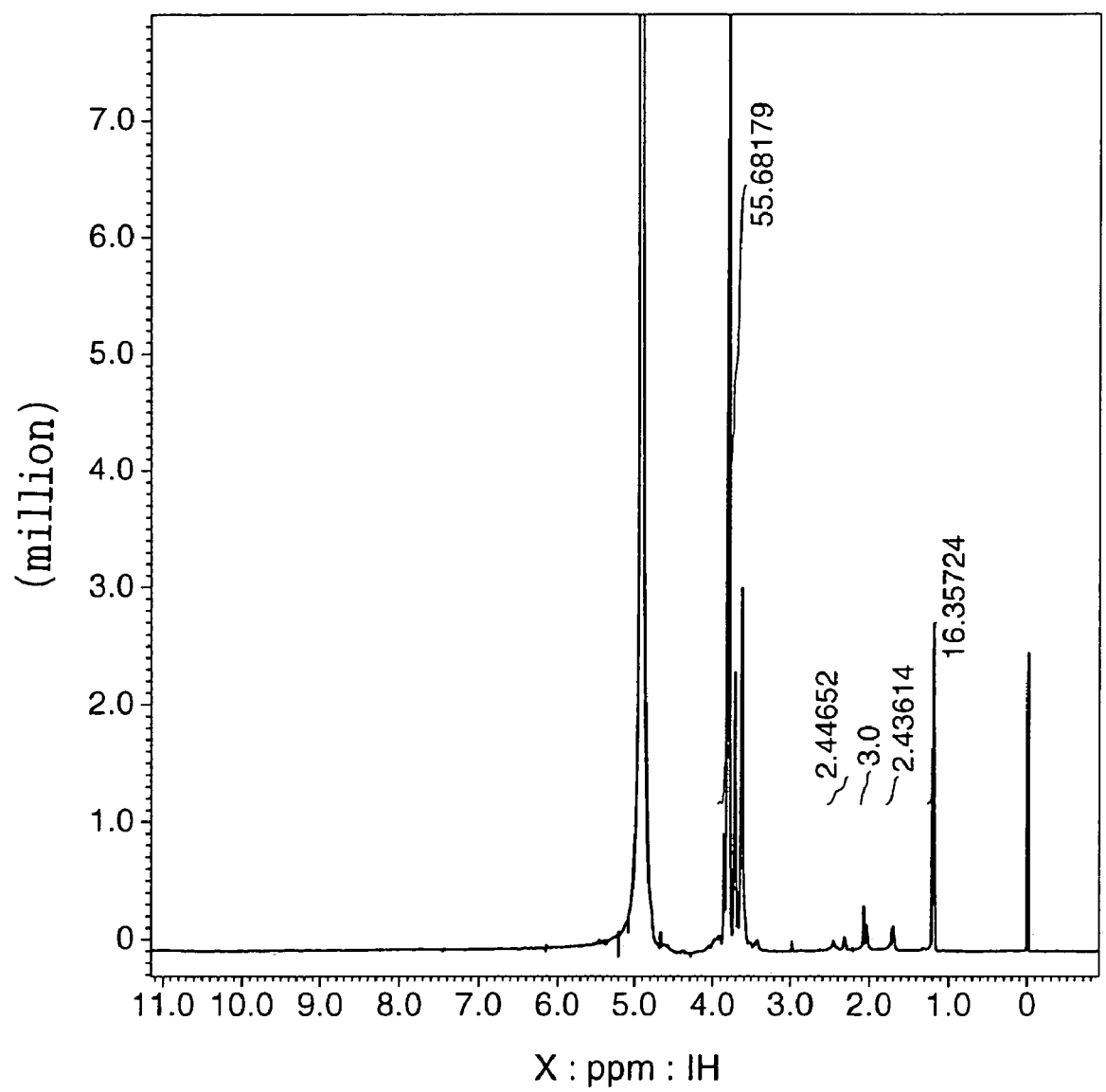
FIG. 10 is the proton NMR chart of the hyaluronic acid modification product obtained in Comparative Example 6.
Figure 11:
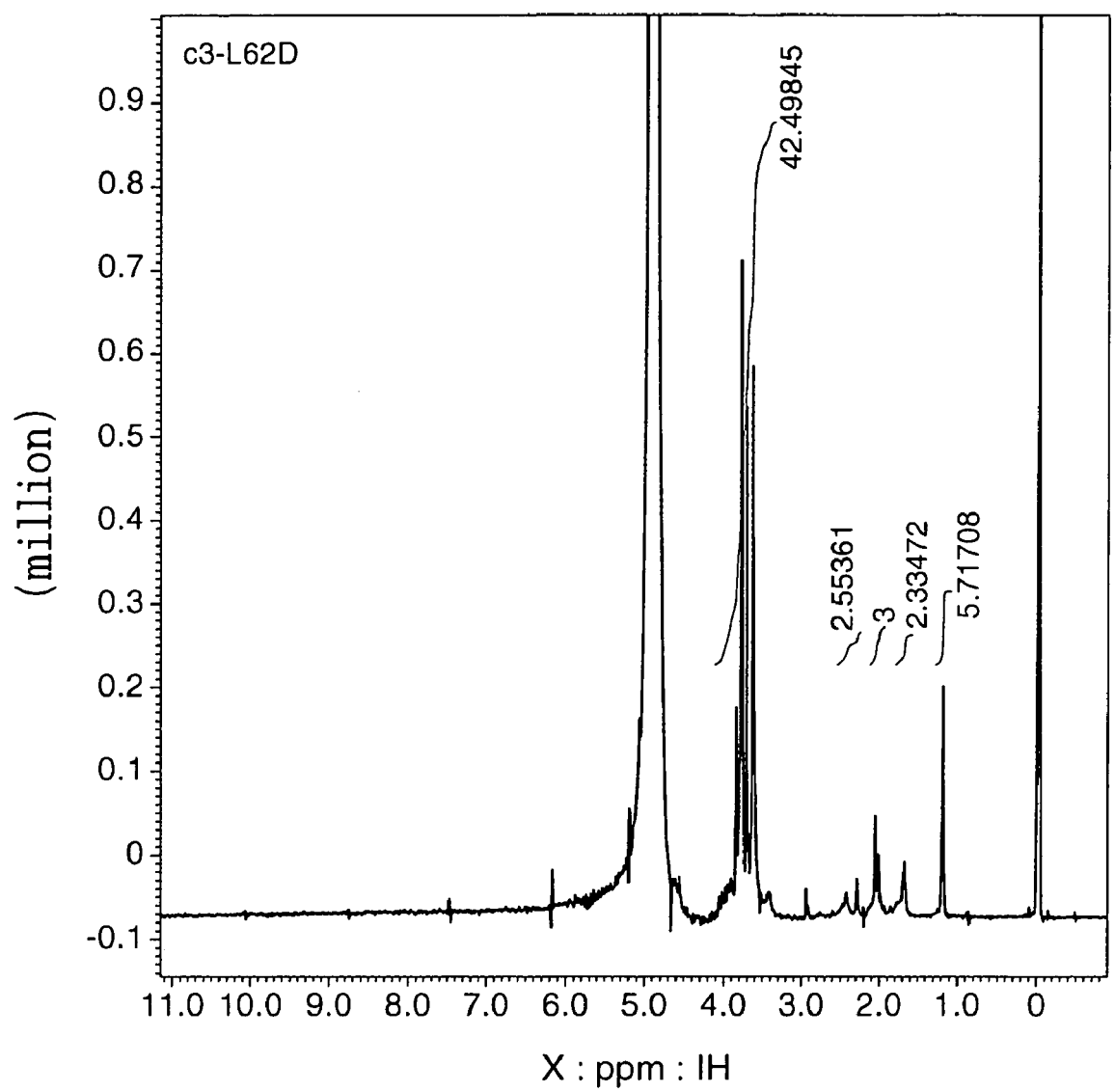
FIG. 11 is the proton NMR chart of the hyaluronic acid modification product obtained in Comparative Example 7.
Figure 12:
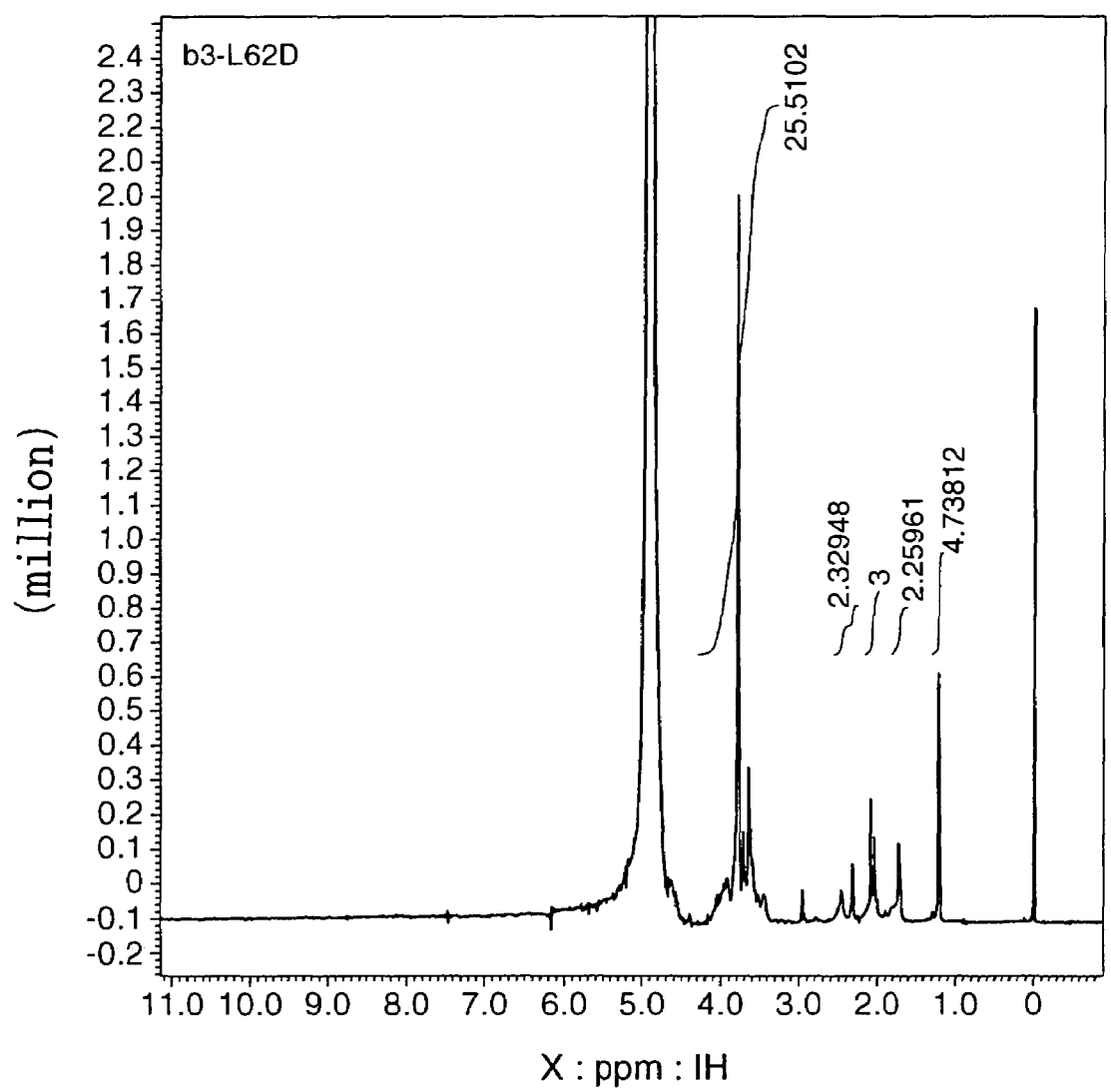
FIG. 12 is the proton NMR chart of the hyaluronic acid modification product obtained in Comparative Example 8.

Hereinbelow, the present invention will be described more specifically.

The hyaluronic acid modification product of the invention is a product in which hyaluronic acid (sometimes abbreviated to "HA") and/or a pharmaceutically acceptable salt thereof is bound to a block polymer selected from polyethylene oxide-polypropylene oxide-polyethylene oxide block polymer, polypropylene oxide-polyethylene oxide-polypropylene oxide block polymer, polyethylene oxide-polylactic acid/polyglycolic acid copolymer-polyethylene oxide block polymer, polylactic acid/polyglycolic acid copolymer-polyethylene oxide-polylactic acid/polyglycolic acid copolymer block polymer, polyethylene oxide-polylactic acid-polyethylene oxide block polymer and polylactic acid-polyethylene oxide-polylactic acid block polymer. Hyaluronic acid is a straight-chained, high molecular weight polysaccharide in which β-D-N-acetylglucosamine and β-D-glucuronic acid are alternately connected, and has the following basic structure.

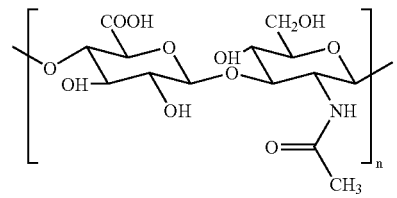

(where n is, though not particularly limited, an integer from 100 to 10,000, for example.)

When the hyaluronic acid modification product of the invention is injected into the living body (e.g. into the joint cavity or the like), it undergoes phase transition at the body temperature and sharply increases its viscoelesticity as a result of the physical cross-inking by hydrophobic bonds associated with the phase transition. That is, the hyaluronic acid modification product of the invention is not in a state of crosslinked gel at temperatures below its phase transition temperature, but in a state of sol with fluidity.

For this purpose, it is desirable in the hyaluronic acid modification product of the invention that the most part of the above-described block polymer is bound to the hyaluronic acid and/or a pharmaceutically acceptable salt thereof at only one end of its two ends. Herein, the expression "the most part of the above-described block polymer is bound to the hyaluronic acid and/or a pharmaceutically acceptable salt thereof at only one end of its two ends" refers to such a state of binding where the fluidity of the resultant hyaluronic acid modification product is retained under normal atmosphere at 20° C. or below (i.e. the resultant hyaluronic modification product is in a state of sol). Further, such a state of binding is preferable where no remarkable difference in viscosity is recognized when the raw material hyaluronic acid and/or pharmaceutically acceptable salt thereof is compared with the resultant hyaluronic acid modification product. The term "the most part" used above does not mean a particularly limited ratio as long as the above-described state of binding is achieved; specifically, the term refers to a state where the amount of the block polymer binding to the hyaluronic acid and/or a pharmaceutically acceptable salt thereof at only one of its two ends is 70% w/w or more, preferably 85% w/w or more, particularly preferably 95% w/w or more, based on the amount of the total block polymer binding thereto. In any case, the ratio of introduction of the both ends of the block polymer into the hyaluronic acid and/or a pharmaceutically acceptable salt thereof is 5 mol % or less, preferably 3 mol % or less, particularly preferably 1 mol % or less, per the glucuronic acid in the hyaluronic acid and/or a pharmaceutically acceptable salt thereof Needless to say, the hyaluronic acid modification product of the invention may solely consists of a hyaluronic acid modification product in which the above-described block polymer is bound to the hyaluronic acid and/or a pharmaceutically acceptable salt thereof at only one of its two ends.

As a method for determining the ratio of the amount the block polymer binding to the hyaluronic acid and/or a pharmaceutically acceptable salt thereof at only one of its two ends to the amount of the total block polymer binding thereto, as well as determining the ratio of introduction of the both ends of the block polymer into the hyaluronic acid and/or a pharmaceutically acceptable salt thereof, the ratio can be obtained by comparing the amount of block polymer introduced obtainable by proton NMR with the amount of actual loss of hydrazide (HZ) or amino group in the hydrazidated or aminated hyaluronic acid and/or a pharmaceutically acceptable salt thereof before the block polymer is bound. For example, when a hydrazidated hyaluronic acid and/or a pharmaceutically acceptable salt thereof is used before the binding of a block polymer, the free hydrazide group-derived peak (2.2-2.3 ppm) obtained from proton NMR of a hyaluronic acid derivative (HA-HZ) into which hydrazide groups were introduced with adipic hydrazide should decrease in proportion to the introduction ratio of the block polymer. Therefore, the ratio of this peak to the hyaluronic acid-derived peak (2.1 ppm) is actually measured (X). On the other hand, on the assumption that 100% of the block polymer is introduced at only one of its two ends, the ratio of the free hydrazide group-derived peak calculated proportionally from the block polymer introduction ratio to the hyaluronic acid-derived peak is calculated (Y). The actually measured ratio may be smaller than the theoretical ratio, and this difference corresponds to the ratio of the block polymer binding at its both ends. Let us suppose that the ratio of introduction of block polymer to glucuronic acid is Z % and the hydrazide group introduction ratio in HA-HZ is H %. Then, the ratio (%) of the amount of block polymer binding to hyaluronic acid and/or a pharmaceutically acceptable salt thereof at only one of its two ends to the amount of the total block polymer binding thereto is represented by the formula $(1-(H-Z)/Z(1-X/Y))\times 100$. Similarly, the ratio (%) of introduction of the both ends of block polymer into hyaluronic acid and/or a pharmaceutically acceptable salt thereof is represented by the formula $(H-Z)\times(1-X/Y)$ per glucuronic acid.

Further, it is desirable that the phase transition temperature of the hyaluronic acid modification product of the invention in physiological saline and/or phosphate physiological saline should be in the range from 20° C. to 35° C. when the concentration of the hyaluronic acid modification product is 10.0% w/v or less. The "phase transition temperature" used herein refers to the temperature at which viscosity change has reached 10% of its maximum change when thermal changes in the viscosity of the hyaluronic modification product are measured with a viscometer such as a cone/plate type viscometer. Therefore, this phase transition may be either the so-called sol-gel transition or a transition from a sol to a sol of still higher viscosity, within a range in which the purpose of the present invention is met.

With respect to the hyaluronic acid and/or a pharmaceutically acceptable salt thereof used in the invention, it is preferred that the weight average molecular weight of the above acid or a salt thereof should be 1,500,000 daltons or less in order to suppress the viscosity at a level suitable for injection and to enable room temperature distribution. The lower limit of the weight average molecular weight thereof is not particularly limited. However, as the weight average molecular weight decreases, a higher hyaluronic acid concentration will be required to achieve viscosity increase attendant upon temperature increase. Therefore, the lower limit is preferably 10,000 daltons or more. As a method for determining the weight average molecular weight of hyaluronic acid and/or a pharmaceutically acceptable salt thereof, various known methods, such as the photo-scattering method, may be used. Such a hyaluronic acid and/or a pharmaceutically acceptable salt thereof may be prepared by various known methods, for example, by extracting organism-derived materials (e.g. from cock's crest or beneath pig skin) or by biofermentation. Alternatively, commercial products may be purchased (e.g. from Denki Kagaku Kogyo, Shiseido, Seikagaku Corporation, etc.).

As pharmaceutically acceptable salts of hyaluronic acid, alkali metal salts such as sodium salts, potassium salts or lithium salts may be enumerated, for example. Of these salts, especially preferred are sodium salts which are often used in pharmaceuticals.

With respect to the block polymer used in the invention selected from polyethylene oxide-polypropylene oxide-polyethylene oxide block polymer (PEO-PPO-PEO), polypropylene oxide-polyethylene oxide-polypropylene oxide block polymer (PPO-PEO-PPO), polyethylene oxide-polylactic acid/polyglycolic acid copolymer-polyethylene oxide block polymer (PEO-PLGA-PEO), polylactic acid/polyglycolic acid copolymer-polypropylene oxide-polylactic acid/polyglycolic acid copolymer block polymer (PLGA-PEO-PLGA), polyethylene oxide-polylactic acid-polyethylene oxide block polymer (PEO-PLA-PEO) and polylactic acid-polyethylene oxide-polylactic acid block polymer (PLA-PEO-PLA), the lower critical solution temperatures (LCSTs) of these polymers in 1.0% w/v physiological saline and/or 1.0% w/v phosphate physiological saline are adjusted so that the phase transition temperature of the hyaluronic modification product of the invention falls within the range from 20° C. to 35° C. Specifically, in 1.0% w/v physiological saline and/or 1.0% w/v phosphate physiological saline (preferably, in 1.0% w/v phosphate physiological saline), the LCST of the above-described block polymer may be in the range from 15° C. to 40° C. The term "LCST" used herein refers to the temperature at which the absorbance change at 500 nm reached 10% of the maximum change when the absorbance of the block polymer dissolved in the above-mentioned solution is measured while changing temperature. Although a plurality of the above block polymers with different LCSTs within the above-mentioned range of transition temperature may be used in combination, it is preferable to use a single block polymer.

The block polymers used in the invention selected from polyethylene oxide-polypropylene oxide-polyethylene oxide block polymer (PEO-PPO-PEO), polypropylene oxide-polyethylene oxide-polypropylene oxide block polymer (PPO-PEO-PPO), polyethylene oxide-polylactic acid/polyglycolic acid copolymer-polyethylene oxide block polymer (PEO-PLGA-PEO), polylactic acid/polyglycolic acid copolymer-polypropylene oxide-polylactic acid/polyglycolic acid copolymer block polymer (PLGA-PEO-PLGA), polyethylene oxide-polylactic acid-polyethylene oxide block polymer (PEO-PLA-PEO) and polylactic acid-polyethylene oxide-polylactic acid block polymer (PLA-PEO-PLA) generally have the following basic structures, though not limited to these structures.

(1) PEO-PPO-PEO Triblock Polymer

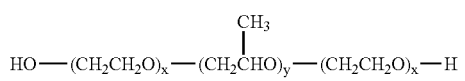

(2) PPO-PEO-PPO Triblock Polymer

(3) PEO-PLGA-PEO Triblock Polymer or PEO-PLA-PEO Triblock Polymer

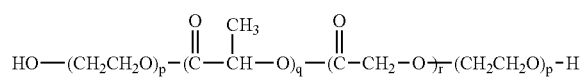

(4) PLGA-PEO-PLGA Triblock Polymer or PLA-PEO-PLA Triblock Polymer

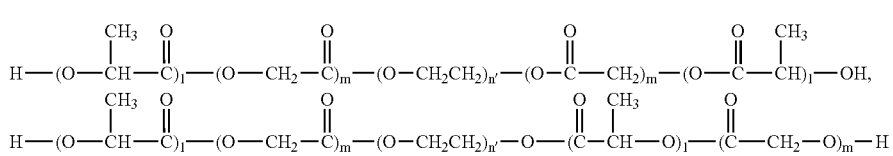

In PEO-PPO-PEO triblock polymer and PPO-PEO-PPO triblock polymer, the ratio of hydrophobic PPO block to hydrophilic PEO block is preferably 90-10% w/w: 10-90% w/w, though not limited to this range. In PEO-PLGA-PEO triblock polymer, PLGA-PEO-PLGA triblock polymer, PEO-PLA-PEO triblock polymer and PLA-PEO-PLA triblock polymer, the ratio of hydrophobic PLGA or PLA block to hydrophilic PEO block is preferably 51-83% w/w: 17-49% w/w, though not limited to this range. In PLGA or PLA block, the lactate content is preferably 30-100 mol %, more preferably 50-100 mol %; and the glycolate content is preferably 0-70%, preferably 0-50%.

In order for the hyaluronic acid modification product of the invention to be able to exhibit sufficient crosslinking strength, the weight average molecular weight of the block polymer is preferably 1200 daltons or more. Further, considering discharge from the living body after biodegradation, a weight average molecular weight of 1200 to 10,000 daltons is more preferable if the block polymer is PEO-PPO-PEO or PPO-PEO-PPO. If PEO-PLGA-PEO, PLGA-PEO-PLGA, PEO-PLA-PEO or PLA-PEO-PLA is used as the block polymer, the weight average molecular weight of the PEO component is preferably 10,000 daltons or below since PLGA or PLA itself is biodegradable. The term "weight average molecular weight" of PEO-PLGA-PEO, PLGA-PEO-PLGA, PEO-PLA-PEO or PLA-PEO-PLA, or PEO used herein means the weight average molecular weight as measured by gel permeation chromatography (GPC) using polyethylene oxide as a standard substance.

Such PEO-PPO-PEO is sold under the product name of Pluronic, and such PPO-PEO-PPO is sold under the product name of Pluronic R. They are available from, for example, BASF-Takeda Vitamins and Asahi Denka Kogyo. A method of synthesis of such polymers is described, for example, in Colloids and Surfaces A, 96, 146 (1995). PEO-PLGA-PEO and PLGA-PEO-PLGA are sold under the product name of Regel; they are available from MacroMed, Alkermes, etc. A method of synthesis of such polymers is described, for example, in J. Biomed. Mat. Res. 61, 188-196 (2002) and WO99/18142.

Methods of binding a block polymer to hyaluronic acid and/or a salt thereof are not particularly limited. For example, hydrazidation (International Patent Publication Number WO95/15168 (U.S. Pat. Nos. 5,616,568; 5,652,347; 5,874,417) etc.); or a method in which hyaluronic acid or a pharmaceutically acceptable salt thereof is aminated by coupling thereto a diamine compound with a coupling agent such as carbodiimide, and then the aminated product and the hydroxyl group at one end of the block polymer are combined with 4-nitrophenyl chloroformate (International Patent Publication Number WO95/24430 (U.S. Pat. No. 6,486,213)); or a method in which a crosslinking agent consisting of di-N-hydroxysuccinimide is reacted in DMSO in the presence of a basic, organic solvent such as pyridine, and then the N-hydroxysuccinimidated block polymer is reacted; or a method in which the block polymer is combined with 4-nitrophenyl chloroformate and then reacted with diamine or dihydrazide to obtain a block polymer modified with an amino or hydrazide group at it one end; this block polymer is bound to the carboxyl group of hyaluronic acid and/or a pharmaceutically acceptable salt thereof using a coupling agent such as carbodiimide, may be enumerated.

For reference, the above-described binding of hyaluronic acid and/or a pharmaceutically acceptable salt thereof to the hydroxyl group at the one end of the block polymer may be shown schematically in the following schemes (1) to (4). However, these schemes are only provided for the purpose of schematically explaining the reaction between polymers. The binding method of the present invention is not limited by these schemes. For example, although hyaluronic acid is expressed as HA-COOH in the following schemes, carboxyl groups in hyaluronic acid are present in the number of the repeat unit ("n" mentioned above) of the basic structure.

Scheme (1)

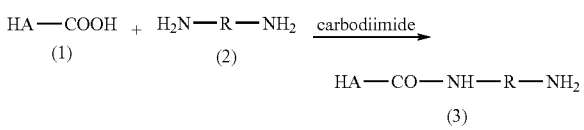

(where HA—COOH represents hyaluronic acid; and $H_2N$—R—$NH_2$ represents dihydrazide or diamine [if R=NH—CO-A-CO—NH, this represents dihydrazide].)

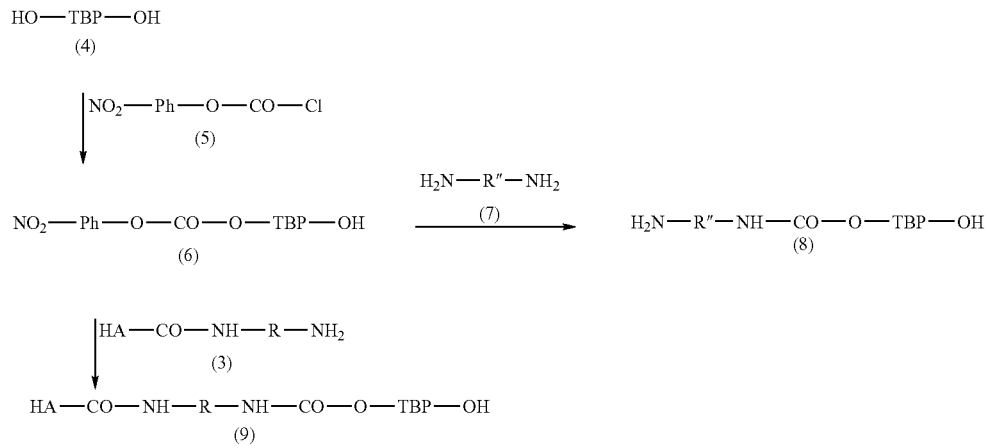

(where HO-TBP-OH represents each triblock polymer described above; Ph represents phenyl; $H_2N$—$R''$—$NH_2$ represents dihydrazide or diamine [if $R''$=NH—CO-A-CO—NH, this represents dihydrazide]; and other abbreviations are as defined above.)

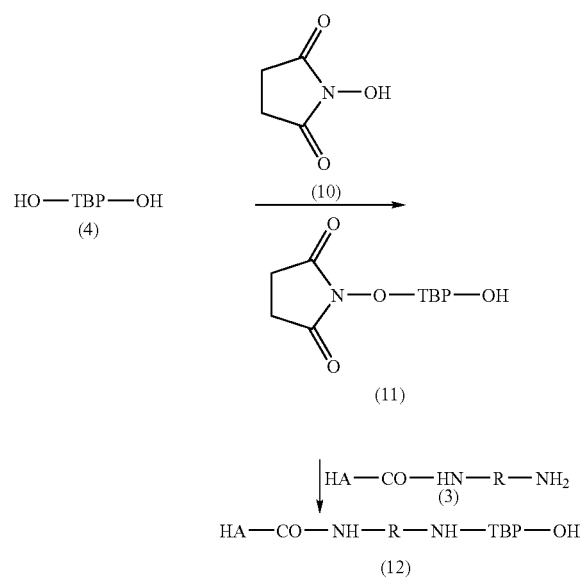

(where abbreviations are as defined above.)

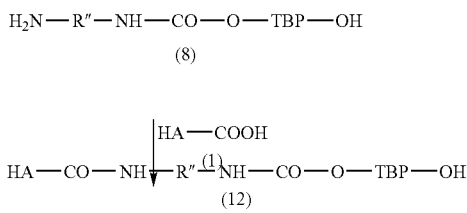

(where abbreviations are as defined above.)

The reaction conditions for the reactions shown in the above schemes may be determined with reference to the description in International Patent Publication Number WO95/15168, International Patent Publication Number WO95/24430, etc. For example, in scheme (1), hyaluronic acid (1) is reacted with dihydrazide (2) in the presence of dicarbodiimide such as dicyclohexylcarbodiimide or dimethylaminopropyl carbodiimide to thereby obtain a terminally aminated hyaluronic acid (3). Usually, this reaction is carried out in water and/or an aqueous solvent (e.g. dimethylformamide, dimethylsulfoxide, alcohols, or diols) at 0-100° C., preferably at 10-40° C., for 0.5-48 hours. In scheme (2), a triblock polymer (4) and 4-nitrophenyl chloroformate (5) are reacted in a halogenated hydrocarbon solvent (such as methyl chloride) in the presence of a base (such as triethylamine) at 0-40° C. for 0.5-24 hours to obtain a 4-nitrophenyl formate bound triblock polymer (6). This compound (6) is reacted with the terminally aminated hyaluronic acid (3) in water and/or an aqueous solvent at 0-40° C. for 0.5-48 hours to thereby obtain a target triblock polymer-coupled hyaluronic acid (9). On the other hand, the compound (6) and diamine (7) are reacted in a halogenated hydrocarbon solvent at 0-40° C. for 0.5-48 hours to thereby obtain a terminally aminated triblock polymer (8). This compound (8) is reacted with the hyaluronic acid (1) to thereby obtain a target triblock polymer-coupled hyaluronic acid (12) (scheme (4)). In scheme (3), the triblock polymer (4) is reacted with N-hydroxysuccinimide (NHS) (10) to thereby obtain an NHS-activated triblock polymer (11), which is then reacted with the terminally aminated hyaluronic acid (3) to thereby obtain a target triblock polymer-coupled hyaluronic acid (12). In the above reactions, a block polymer the most part of which has an activated functional group introduced into only the hydroxyl group at one end can be obtained easily by adjusting the amounts of individual raw materials added to the reaction. For example, it is possible to obtain a block polymer activated at only one of its two ends as a main component by adding an activated functional group to the reaction in an equimolar amount or less relative to the terminal functional group in the block polymer. Further, when the amount of addition of the activated functional group to the reaction is reduced, the ratio of inactivated block polymer increases and, at the same time, the ratio of block polymer which is activated at only one of its two ends also increases.

The diamine and dihydrazide used in the invention are not particularly limited. Specific examples of suitable diamine include diaminoalkanes such as diaminoethane, diaminopropane; mono- or di(lysyl)diaminoalkanes such as N-lysyl-diaminoethane, N,N'-dilysyl-diaminoethane; and peptides with two or more amino groups. Specific examples of suitable dihydrazide include succinic dihydrazide, adipic dihydrazide, suberic dihydrazide, oxalic dihydrazide and malonic dihydrazide. Those which have a hydrophobic portion such as PLGA or PPO at their end are low in graft-reactivity with hyaluronic acid or a derivative thereof in water. Therefore, it is preferable that hyaluronic acid or a derivative thereof should be converted into a tributylammonium salt soluble in a polar organic solvent such as DMSO and that the above reaction should be performed in a polar organic solvent. If the above process includes hydrazidation, it is desirable, from the viewpoint of application to the living body, to react the unreacted hydrazide groups remaining in the hyaluronic acid modification product of the invention with succinic anhydride or the like to eliminate free hydrazide groups.

With respect to the ratio of introduction of the above-described block polymer into hyaluronic acid and/or a pharmaceutically acceptable salt thereof, it is preferred that the ratio should be at least 8 mol % per the glucuronic acid in the hyaluronic acid in order to obtain sufficient viscosity change attendant upon phase transition. The ratio of introduction of the above-described block polymer into hyaluronic acid and/or a pharmaceutically acceptable salt thereof may be determined by proton NMR method; specifically, the ratio may be calculated from the area ratio of a hyaluronic acid-derived proton (N-acetylate) to a proton derived from the above-described block polymer.

The hyaluronic acid modification product of the invention thus obtained is capable of room temperature distribution since high molecular weight hyaluronic acid is not used therein. Besides, by adjusting the phase transition temperature to fall within the range from 20° C. to 35° C., this hyaluronic acid modification product becomes easy to handle (i.e. easy to inject) due to its low viscosity at room temperature. On the other hand, when injected into the living body (e.g. into the joint cavity), the hyaluronic acid modification product is warmed up to its phase transition temperature and thus its viscoelesticity increases sharply.

When injected into the living body (e.g. into the joint cavity), the hyaluronic acid modification product of the invention is desired to reside there for a long period of time. The term "long period of time" used herein means a period that conventional hyaluronic acid preparations could not have achieved, i.e., one week or more, preferably two weeks or more. In order to measure its residence time in the living body (e.g. in the joint cavity), methods which have been tried with conventional hyaluronic acid preparations, such as a method in which radioactively labeled hyaluronic acid is used (Japanese Pharmacology and Therapeutics, 22, 325-350, 1994) or a method in which hyaluronic acid labeled with a fluorescent label such as fluoresceine isothiocyanate (FITC) is used, may be employed. Alternatively, a method in which the hyaluronic acid moiety is degraded with hyaluronidase and then the block polymer is determined by GPC; or a method in which the time course (decrease) of the joint width after administration of the hyaluronic acid modification product is measured directly may be used.

As described above, the hyaluronic acid modification product of the invention is capable of room temperature distribution, easy to inject because of its low viscosity, and capable of residing in the joint cavity for a long period of time (two weeks or more). Besides, it is expected to be highly safe. Therefore, the hyaluronic acid modification product of the invention is very useful in treating joint diseases as a main component of novel and practical hyaluronic acid preparations.

The "joint diseases" used herein refers to diseases such as loss of articular cartilage, rheumatoid arthritis, osteoarthritis, scapulo-humeral periarthritis and so on. The term "treating" used herein refers to treatment for curing or preventing joint diseases and for inhibiting the progress of conditions (i.e. prevention of worsening, or maintaining the existing status).

In view of the above-described properties of the hyaluronic acid modification product of the invention, it is possible to apply this product to assisting or treating agents for use in surgical operation, carriers for sustained release drugs, or cell proliferation matrixes for use in regeneration medicine or tissue engineering. For example, an assisting or treating agent for surgical operation comprising the hyaluronic modification product of the invention as its main component may be used in ophthalmic surgery or endoscopic mucosal resection (EMR) (see, for example, WO02/056914). Further, the hyaluronic acid modification product of the invention is also applicable to use for repairing damage to soft tissue (see Japanese Unexamined Patent Publication No. 10-324701). For example, the hyaluronic acid modification product of the invention may be used safely for repairing damage to soft tissue (e.g. acne scars), atrophic irregularity after surgical operation, damage caused by Mohs' chemosurgical treatment, damage such as laceration scars in lips and old-age wrinkles, or wrinkles themselves.

The hyaluronic acid modification product of the invention may be used as a pharmaceutical composition comprising an effective amount of this product and, optionally, a pharmaceutically acceptable carrier, excipient, disintegrant, binder, aromatic and coloring agent. The pharmaceutical composition of the invention may be formulated into injections, liquids, percutaneous absorbents, ointments, lotions, capsules, etc. The content of hyaluronic acid of such a preparation is 0.01-99.9% w/w, preferably 0.1-70% w/w, relative to the total preparation.

When the hyaluronic acid modification product of the invention is formulated into a preparation for treating joint diseases or an assisting or treating agent for surgical operation, the formulation method is not particularly limited. For example, the hyaluronic acid modification product of the invention may be dissolved in physiological saline or phosphate physiological saline at a desired concentration and formulated into an injection. If necessary, the pH of the solution may be adjusted to a desired pH by addition of acid or base. Further, the solution may be adjusted to have a desired salt concentration by adding thereto inorganic salts such as monovalent metal salts (e.g. sodium salts, potassium salts) or divalent metal salts (e.g. magnesium salts, calcium salts, manganese salts). Further, if desired, a stabilizer or the like may also be added. The thus prepared solution of the hyaluronic acid modification product of the invention may be filled in syringes (such as disposable syringes) in advance and then distributed.

When a preparation for treating joint diseases comprising the hyaluronic acid modification product of the invention as its main component is administered as an injection, the injection may be administered to patients in an amount of 1-3 ml per administration, wherein the concentration of the hyaluronic acid modification product of the invention in the injection is 0.01-50% w/v, preferably 0.05-20% w/v, particularly preferably 0.5-10% w/v. However, this dosage may be appropriately increased or decreased depending on doctor's instructions, patients to be treated, diseases or severity of diseases, or the molecular weight of the raw material hyaluronic acid, etc.

When an assisting or treating agent for surgical operation comprising the hyaluronic acid modification product of the invention as its main component is used as an injection, a necessary amount of the injection may be applied to the target site of the operation, wherein the concentration of the hyaluronic acid modification product of the invention in the injection is 0.01-50% w/v, preferably 0.05-20% w/v, particularly preferably 0.5-10% w/v. For example, it is possible to apply such a preparation to the target site of the operation using an endoscopic injection needle which is 20-22 G in diameter and has a tube 1000-2500 mm in the effective length; thus, the preparation may be utilized for the resection of mucosal tissue in the stomach, intestine, etc. For example, the preparation is applied to the submucosal layer at the target site of intended resection of polyp or tumor, through an endoscopic injection needle so that the target site is elevated. Then, this elevated portion is resected with a snare or needle knife. When the above-mentioned preparation is used as an assisting agent for ophthalmic surgery, e.g. cataract operation, the preparation is injected for the purposes of maintaining the space for operation (called the "depth of the anterior chamber") and protecting the corneal endothelium, etc. from physical invasion. For example, after removal of the turbid nucleus of lens, by injecting the above-described preparation, it is possible to insert an intraocular lens while maintaining the depth of the anterior chamber sufficiently.

The tissue repairing agent of the invention may be applied to a site where tissue repairing is needed, in the form of a preparation such as injection, liquid, percutaneous absorbent, ointment or lotion having the above-described composition.

EXAMPLES

Hereinbelow, the present invention will be described more specifically with reference to preferred Examples of the invention. However, the present invention is not limited to these Examples.

In the following Examples, NMR spectra were measured using a nuclear magnetic resonance apparatus JNM-ECA500 (JEOL Ltd).

Example 1

Example 1-1

(1) Synthesis of Nitrophenyl Formate Bound Pluronic L62D (Pluronic L62D-NPC)

Eight (8) millimoles of Pluronic L62D (product name) (molecular weight: 2360 daltons; LCST: 28° C.; manufactured by BASF-Takeda Vitamins) and 10 mmol of 4-N-nitrophenyl chloroformate (manufactured by Tokyo Kasei) were dissolved in 100 ml of methylene chloride (Sigma). To this solution, 10 mmol of triethylamine was added and reacted at room temperature for 12 hours. The reaction solution was washed with ether and then concentrated in an evaporator to thereby obtain 17.2 g of Nitrophenyl formate bound Pluronic L62D (Pluronic L62D-NPC).

(2) Synthesis of Hydrazide (HZ) Group-Introduced Hyaluronic Acid (HA-HZ)

One hundred (100) milligrams of hyaluronic acid (HA) with a molecular weight of $5.8 \times 10^5$ daltons (manufactured by Denki Kagaku Kogyo) was dissolved in distilled water at a concentration of 0.25%. The pH of this solution was adjusted to 4.7-4.8 with 5 N HCl. Then, 1-ethyl-3-3-dimethylaminopropyl carbodiimide (EDC) and adipic dihydrazide (ADH) were added thereto to give a molar ratio of HA:EDC:ADH=1:5:40. The resultant solution was subjected to a reaction at room temperature for two hours while maintaining the pH at 4.7-4.8 with 5 N HCl. Then, the solution was dialyzed against 100 mM sodium chloride solution and 25% ethanol solution (Spectrapore #7; molecular weight cut off (MWCO): 12 k-14 k daltons), followed by lyophilization to thereby obtain 85 mg of the above-mentioned hydrazide (HZ) group-introduced hyaluronic acid (HA-HZ).

The HZ introduction ratio in the resultant HA-HZ was determined by proton NMR method. The results revealed that HZ was introduced into 68% of the carboxylic acid of the HA (HA: N-acetylate, 2.1 ppm; HZ: methylene, 1.7 ppm, 2.4 ppm).

(3) Synthesis of Hyaluronic Acid Modification Product in which PEO-PPO-PEO is Bound to Hyaluronic Acid Ten (10) milligrams of HA-HZ obtained in (2) above was dissolved in 10 ml of 100 mM phosphate buffer (PB, pH 8.0). To this solution, Pluronic L62D-NPC obtained in (1) above was added to give a molar ratio of HZ:NPC=1:20. The resultant solution was subjected to a reaction at 4° C. for one day. The pH was adjusted to 11 and the excessive NPC was hydrolyzed. Then, the resultant solution was dialyzed against water at 4° C. (Spectrapore #7, MWCO: 300 k daltons) for purification and concentrated by evaporation. Thus, the subject hyaluronic acid modification product in which a polyethylene oxide-polypropylene oxide-polyethylene oxide block polymer (PEO-PPO-PEO) is bound to hyaluronic acid was obtained.

The Pluronic introduction ratio in the resultant HA-Pluronic was determined by proton NMR method. The results revealed that Pluronic was introduced into 13 mol % of the carboxylic acid of the HA (HA: N-acetylate, 2.1 ppm; Pluronic: methyl of propyleneoxide, 1.2 ppm).

A 4% v/v solution of this hyaluronic acid modification product in phosphate physiological saline was liquid at 25° C. and became gel at 36° C.

Example 1-2

(1) Synthesis of HZ-Introduced Hyaluronic Acid (HA-HZ)

The subject HZ-introduced HA (HA-HZ) (83 mg) was obtained in the same manner as described in (2) in Example 1-1 above except that 100 mg of HA with a molecular weight of $1.9 \times 10^5$ daltons (Denki Kagaku Kogyo) was dissolved in distilled water at a concentration of 0.5%. The HZ introduction ratio in the resultant HA-HZ was determined by proton NMR method. The results revealed that HZ was introduced into 64% of the carboxylic acid of the HA (HA: N-acetylate, 2.1 ppm; HZ: methylene, 1.7 ppm, 2.4 ppm).

(2) Synthesis of Hyaluronic Acid Modification Product in which PEO-PPO-PEO is Bound to Hyaluronic Acid Ten (10) milligrams of HA-HZ obtained in (1) above was dissolved in 10 ml of 100 mM phosphate buffer (PB, pH 8.0). To this solution, Pluronic L62D-NPC obtained in the same manner as described in (1) in Example 1-1 was added to give a molar ratio of HZ:NPC=1:20. The resultant solution was subjected to a reaction at 4° C. for one day. The pH was adjusted to 11 and the excessive NPC was hydrolyzed. Then, the resultant solution was dialyzed against water at 4° C. (Spectrapore #7, MWCO: 300 k daltons) for purification and concentrated by evaporation. Thus, the subject hyaluronic acid modification product in which PEO-PPO-PEO is bound to hyaluronic acid was obtained.

The Pluronic introduction ratio in the resultant HA-Pluronic was determined by proton NMR method. The results revealed that Pluronic was introduced into 30 mol % of the carboxylic acid of the HA (HA: N-acetylate, 2.1 ppm; Pluronic: methyl of propyleneoxide, 1.2 ppm).

A 6% v/v solution of this hyaluronic acid modification product in phosphate physiological saline was liquid at 25° C. and became gel at 36° C.

Example 1-3

(1) Synthesis of HZ-Introduced Hyaluronic Acid (HA-HZ)

The subject HZ-introduced HA (HA-HZ) (88 mg) was obtained in the same manner as described in (2) in Example 1-1 above except that 100 mg of HA with a molecular weight of $2.5 \times 10^4$ daltons (Denki Kagaku Kogyo) was dissolved in distilled water at a concentration of 1%. The HZ introduction ratio in the resultant HA-HZ was determined by proton NMR method. The results revealed that HZ was introduced into 65% of the carboxylic acid of the HA (HA: N-acetylate, 2.1 ppm; HZ: methylene, 1.7 ppm, 2.4 ppm).

(2) Synthesis of Hyaluronic Acid Modification Product in which PEO-PPO-PEO is Bound to Hyaluronic Acid Ten (10) milligrams of HA-HZ obtained in (1) above was dissolved in 10 ml of 100 mM phosphate buffer (PB, pH 8.0). To this solution, Pluronic L62D-NPC obtained in the same manner as described in (1) in Example 1-1 was added to give a molar ratio of HZ:NPC=1:20. The resultant solution was subjected to a reaction at 4° C. for one day. The pH was adjusted to 11 and the excessive NPC was hydrolyzed. Then, the resultant solution was dialyzed against water at 4° C. (Spectrapore #7, MWCO: 50 k daltons), then against dimethylsulfoxide (DMSO) and finally against water. The resultant solution was lyophilized to thereby obtain the subject hyaluronic acid modification product in which PEO-PPO-PEO is bound to hyaluronic acid.

A 10% v/v solution of this hyaluronic acid modification product in phosphate physiological saline was liquid at 25° C. and became gel at 36° C.

Example 2

Example 2-1

(1) Synthesis of Nitrophenyl Formate Bound Pluronic L92 (Pluronic L92-NPC)

Nitrophenyl formate bound Pluronic L92 (Pluronic L92-NPC) (27.3 mg) was obtained in the same matter as described in (1) in Example 1-1 except that Pluronic L92 (product name) (molecular weight: 3650 daltons; LCST: 17° C.; manufactured by BASF-Takeda Vitamins) and 10 mmol of 4-N-nitrophenyl chloroformate (manufactured by Tokyo Kasei) was used.

(2) Synthesis of Hyaluronic Acid Modification Product in which PPO-PEO-PPO is Bound to Hyaluronic Acid Using the HA-HZ obtained in (2) in Example 1-1, the subject hyaluronic acid modification product in which a polypropylene oxide-polyethylene oxide-polypropylene oxide block polymer (PPO-PEO-PPO) is bound to hyaluronic acid was obtained in the same manner as described in (3) in Example 1-1 except that Pluronic L92-NPC obtained in (1) above was used instead of Pluronic L62D-NPC. The Pluronic introduction ratio in the resultant HA-Pluronic was determined by proton NMR method. The results revealed that Pluronic was introduced into 27 mol % of the carboxylic acid of the HA (HA: N-acetylate, 2.1 ppm; Pluronic: methyl of propyleneoxide, 1.2 ppm).

A 2% v/v solution of this hyaluronic acid modification product in phosphate physiological saline was liquid at 25° C. and became gel at 36° C.

Example 2-2

A target hyaluronic acid modification product in which PPO-PEO-PPO is bound to hyaluronic acid was obtained in the same manner as described in (2) in Example 2-1 except that the HA-HZ obtained in (1) in Example 1-2 was used. The Pluronic introduction ratio in the resultant HA-Pluronic was determined by proton NMR method. The results revealed that Pluronic was introduced into 29 mol % of the carboxylic acid of the HA (HA: N-acetylate, 2.1 ppm; Pluronic: methyl of propyleneoxide, 1.2 ppm).

A 4% v/v solution of this hyaluronic acid modification product in phosphate physiological saline was liquid at 25° C. and became gel at 36° C.

Example 2-3

A target hyaluronic acid modification product in which PPO-PEO-PPO is bound to hyaluronic acid was obtained in the same manner as described in (2) in Example 2-1 except that the HA-HZ obtained in (1) in Example 1-3 was used.

A 10% v/v solution of this hyaluronic acid modification product in phosphate physiological saline was liquid at 25° C. and became gel at 36° C.

Example 2-4

(1) Synthesis of Hydrazide (HZ) Group-Introduced Hyaluronic Acid (HA-HZ)

One hundred (100) milligrams of hyaluronic acid (HA) with a molecular weight of $1.5 \times 10^6$ daltons (manufactured by Denki Kagaku Kogyo) was dissolved in distilled water at a concentration of 0.1%. The pH of this solution was adjusted to 4.7-4.8 with 5 N HCl. Then, 1-ethyl-3-3-dimethylaminopropyl carbodiimide (EDC) and adipic dihydrazide (ADH) were added thereto to give a molar ratio of HA:EDC:ADH=1:5:40. The resultant solution was subjected to a reaction at room temperature for two hours while maintaining the pH at 4.7-4.8 with 5 N HCl. Then, the solution was dialyzed against 100 mM sodium chloride solution and 25% ethanol solution (Spectrapore #7; molecular weight cut off (MWCO): 12 k-14 k daltons), followed by lyophilization to thereby obtain 88 mg of the subject hydrazide (HZ) group-introduced hyaluronic acid (HA-HZ).

The HZ introduction ratio in the resultant HA-HZ was determined by proton NMR method. The results revealed that HZ was introduced into 61% of the carboxylic acid of the HA (HA: N-acetylate, 2.1 ppm; HZ: methylene, 1.7 ppm, 2.4 ppm).

(2) Synthesis of Hyaluronic Acid Modification Product in which PPO-PEO-PPO is Bound to Hyaluronic Acid The subject hyaluronic acid modification product in which PPO-PEO-PPO is bound to hyaluronic acid was obtained in the same manner as described in (2) in Example 2-1 except that the HA-HZ obtained in (1) in Example 2-4 was used. Then, the resultant solution was dialyzed against water at 4° C. (Spectrapore #7, MWCO: 300 k daltons) for purification and concentrated by evaporation. The Pluronic introduction ratio in the resultant HA-Pluronic was determined by proton NMR method. The results revealed that Pluronic was introduced into 9 mol % of the carboxylic acid of the HA (HA: N-acetylate, 2.1 ppm; Pluronic: methyl of propyleneoxide, 1.2 ppm).

A 1% v/v solution of this hyaluronic acid modification product in phosphate physiological saline was liquid at 25° C. and became gel at 36° C.

Comparative Example 1

A hyaluronic acid modification product in which PEO-PPO-PEO is bound to hyaluronic acid was obtained in the same manner as described in Example 1-1 except that Pluronic L-31 (product name) (molecular weight: 1100 daltons; LCST: 39° C.; manufactured by Asahi Denka Kogyo) was used. The Pluronic introduction ratio in the resultant HA-Pluronic was determined by proton NMR method. The results revealed that Pluronic was introduced into 1.4 mol % of the carboxylic acid of the HA (HA: N-acetylate, 2.1 ppm; Pluronic: methyl of propyleneoxide, 1.2 ppm).

A 2% v/v solution of this hyaluronic acid modification product in phosphate physiological saline was liquid at 25° C. and became opaque and whitish at 36° C. However, no remarkable increase in viscosity or gelation was recognized.

Comparative Example 2

A hyaluronic acid modification product in which PEO-PPO-PEO is bound to hyaluronic acid was obtained in the same manner as described in Example 1-2 except that Pluronic L-31 (product name) (molecular weight: 1100 daltons; LCST: 39° C.; manufactured by Asahi Denka Kogyo) was used. The Pluronic introduction ratio in the resultant HA-Pluronic was determined by proton NMR method. The results revealed that Pluronic was introduced into 0.5 mol % of the carboxylic acid of the HA (HA: N-acetylate, 2.1 ppm; Pluronic: methyl of propyleneoxide, 1.2 ppm).

A 4% v/v solution of this hyaluronic acid modification product in phosphate physiological saline was liquid at 25° C. and became opaque and whitish at 36° C. However, no remarkable increase in viscosity or gelation was recognized.

Comparative Example 3

A hyaluronic acid modification product in which PEO-PPO-PEO is bound to hyaluronic acid was obtained in the same manner as described in Example 1-3 except that Pluronic L-31 (product name) (molecular weight: 1100 daltons; LCST: 39° C.; manufactured by Asahi Denka Kogyo) was used. The Pluronic introduction ratio in the resultant HA-Pluronic was determined by proton NMR method. The results revealed that Pluronic was introduced into 2.0 mol % of the carboxylic acid of the HA (HA: N-acetylate, 2.1 ppm; Pluronic: methyl of propyleneoxide, 1.2 ppm).

A 10% v/v solution of this hyaluronic acid modification product in phosphate physiological saline was liquid at 25° C. and became opaque and whitish at 36° C. However, no remarkable increase in viscosity or gelation was recognized.

Comparative Example 4

A hyaluronic acid modification product in which PEO-PPO-PEO is bound to hyaluronic acid was obtained in the same manner as described in Example 1-1 except that Pluronic L-64 (product name) (molecular weight: 2900 daltons; LCST: 54° C.; manufactured by Asahi Denka Kogyo) was used. The Pluronic introduction ratio in the resultant HA-Pluronic was determined by proton NMR method. The results revealed that Pluronic was introduced into 11 mol % of the carboxylic acid of the HA (HA: N-acetylate, 2.1 ppm; Pluronic: methyl of propyleneoxide, 1.2 ppm).

A 2% v/v solution of this hyaluronic acid modification product in phosphate physiological saline was liquid at 25° C. and still liquid at 36° C., and became gel at 55° C.

Comparative Example 5

A hyaluronic acid modification product in which PEO-PPO-PEO is bound to hyaluronic acid was obtained in the same manner as described in Example 1-2 except that Pluronic L-64 (product name) (molecular weight: 2900 daltons; LCST: 54° C.; manufactured by Asahi Denka Kogyo) was used. The Pluronic introduction ratio in the resultant HA-Pluronic was determined by proton NMR method. The results revealed that Pluronic was introduced into 15 mol % of the carboxylic acid of the HA (HA: N-acetylate, 2.1 ppm; Pluronic: methyl of propyleneoxide, 1.2 ppm).

A 4% v/v solution of this hyaluronic acid modification product in phosphate physiological saline was liquid at 25° C. and still liquid at 36° C., and became gel at 54° C.

Comparative Example 6

A hyaluronic acid modification product in which PEO-PPO-PEO is bound to hyaluronic acid was obtained in the same manner as described in Example 1-3 except that Pluronic L-64 (product name) (molecular weight: 2900 daltons; LCST: 54° C.; manufactured by Asahi Denka Kogyo) was used. The Pluronic introduction ratio in the resultant HA-Pluronic was determined by proton NMR method. The results revealed that Pluronic was introduced into 19 mol % of the carboxylic acid of the HA (HA: N-acetylate, 2.1 ppm; Pluronic: methyl of propyleneoxide, 1.2 ppm).

A 10% v/v solution of this hyaluronic acid modification product in phosphate physiological saline was liquid at 25° C. and still liquid at 36° C., and became gel at 55° C.

Comparative Example 7

A hyaluronic acid modification product in which PEO-PPO-PEO is bound to hyaluronic acid was obtained in the same manner as described in Example 1-1 except that Pluronic L62D-NPC was added to give a molar ratio of HZ:NPC=1:2. The Pluronic introduction ratio in the resultant HA-Pluronic was determined by proton NMR method. The results revealed that Pluronic was introduced into 7.0 mol % of the carboxylic acid of the HA (HA:N-acetylate, 2.1 ppm; Pluronic: methyl of propyleneoxide, 1.2 ppm).

A 2% v/v solution of this hyaluronic acid modification product in phosphate physiological saline was liquid at 25° C. No remarkable increase in viscosity or gelation was recognized even at 36° C.

Comparative Example 8

A hyaluronic acid modification product in which PEO-PPO-PEO is bound to hyaluronic acid was obtained in the same manner as described in Example 1-2 except that Pluronic L62D-NPC was added to give a molar ratio of HZ:NPC=1:2. The Pluronic introduction ratio in the resultant HA-Pluronic was determined by proton NMR method. The results revealed that Pluronic was introduced into 5.8 mol % of the carboxylic acid of the HA (HA: N-acetylate, 2.1 ppm; Pluronic: methyl of propyleneoxide, 1.2 ppm).

A 4% v/v solution of this hyaluronic acid modification product in phosphate physiological saline was liquid at 25° C. No remarkable increase in viscosity or gelation was recognized even at 36° C.

Test Example 1

Thermal Responsiveness In Relation To Viscosity

Figure 13:
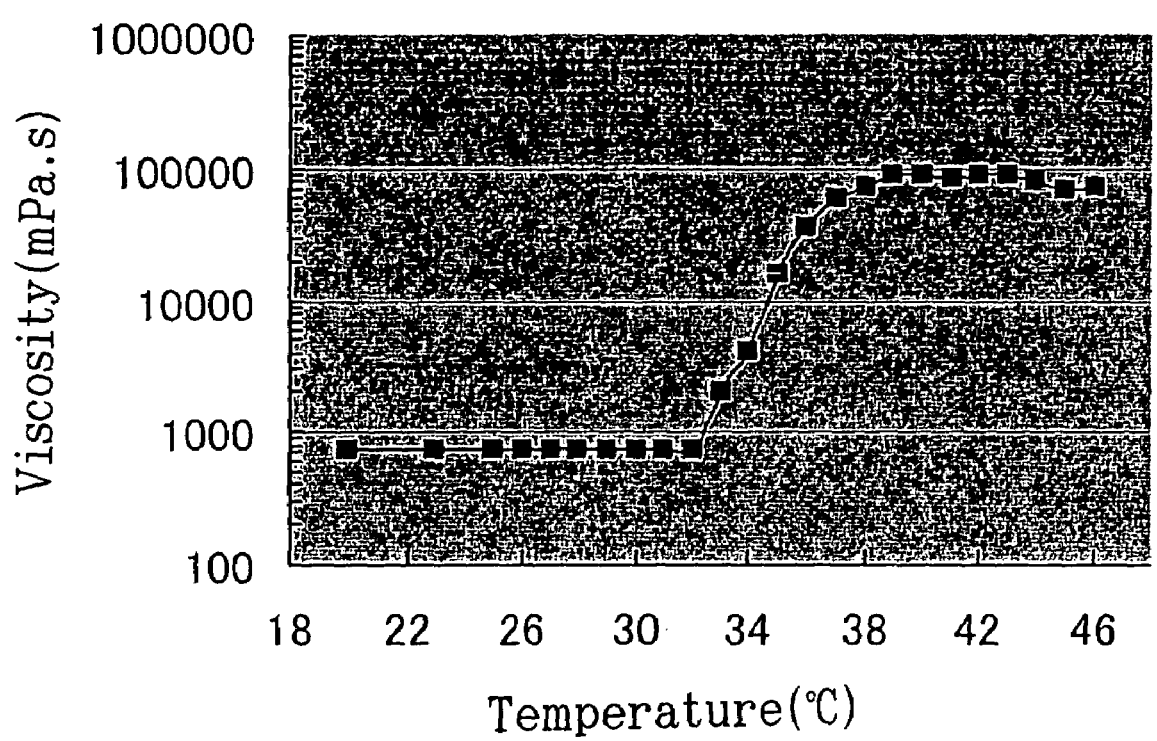
FIG. 13 shows the thermal responsiveness of the viscosity in the hyaluronic acid modification product from Example 2-4, measured in Test Example 1.

The thermal dependency of the viscosity of the 1% v/v solution in phosphate physiological saline described in Example 2-4 was measured using cone/plate type Viscometer RE110R system (Tohki Sangyo) at a shear rate of 1.0 (sec$^{-1}$). As a result, the viscosity at 37° C. was more than 100 times that at the room temperature. The results are shown in FIG. 13.

Test Example 2

Residence in Joint Cavity

Figure 14:
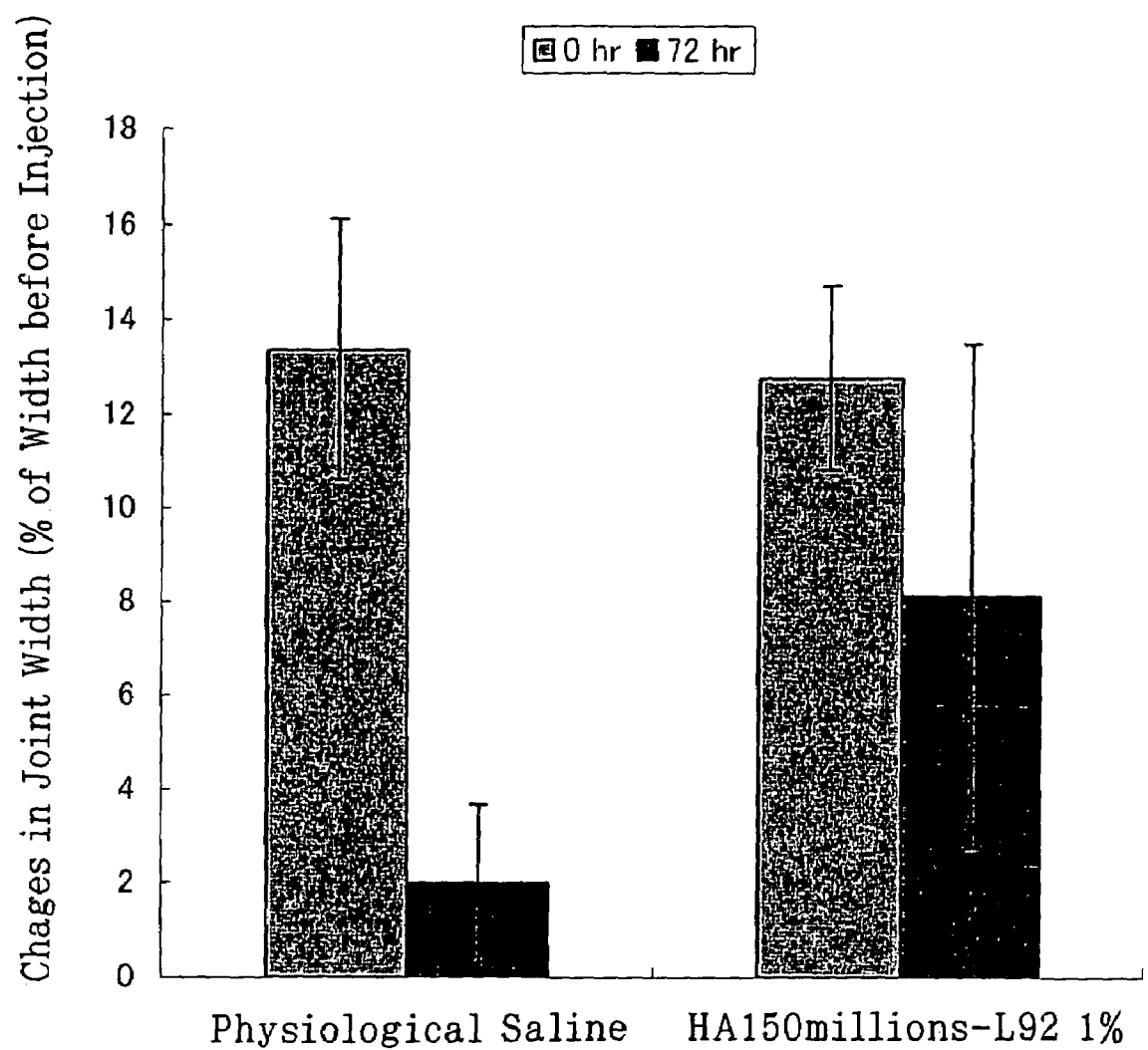
FIG. 14 shows the time course of the joint width after administration of the hyaluronic acid modification product from Example 2-4, measured in Test Example 1.

The legs of etherized rats were shaved. The sample prepared in Example 2-4 was injected into the joint cavity and beneath the skin using a syringe with 26G needle. After this administration, the knee joint width in each rat was measured with a slide caliper at specific time points. The degree of swelling from the knee joint width before the administration was taken as an indicator for the residing property of the administered sample. The knee joint width was measured three times at each point, and the average was used as the representative value at the relevant time point. Even 72 hours after the administration, the knee joint width of the sample-administered rats was more than three times greater than that of physiological saline-administered rats. The results are shown in FIG. 14.

INDUSTRIAL APPLICABILITY

The hyaluronic acid modification product of the invention in which hyaluronic acid and/or a pharmaceutically acceptable salt thereof is bound to a block polymer selected from polyethylene oxide-polypropylene oxide-polyethylene oxide block polymer (PEO-PPO-PEO), polypropylene oxide-polyethylene oxide-polypropylene oxide block polymer (PPO-PEO-PPO), polyethylene oxide-polylactic acid/polyglycolic acid copolymer-polyethylene oxide block polymer (PEO-PLGA-PEO), polylactic acid/polyglycolic acid copolymer-polypropylene oxide-polylactic acid/polyglycolic acid copolymer block polymer (PLGA-PEO-PLGA), polyethylene oxide-polylactic acid-polyethylene oxide block polymer (PEO-PLA-PEO) and polylactic acid-polyethylene oxide-polylactic acid block polymer (PLA-PEO-PLA) is capable of flow at room temperature and has a low viscosity; thus, the hyaluronic acid modification product is easy to handle. However, the product is capable of sharply increasing its viscoelasticity when injected into the living body (e.g. joint cavity). Therefore, the hyaluronic acid modification product of the invention is very useful in treating joint diseases as a main component for novel and practical hyaluronic acid preparations. Further, pharmaceutical preparations comprising the hyaluronic modification product of the invention as their main component may also be used effectively as assisting or treating agents for surgical operation such as ophthalmic surgery or endoscopic mucosal resection. Further, in view of the properties of the hyaluronic acid modification product of the invention, the product is expected to be applicable to a carrier for sustained release drugs.

What is claimed is:

1. A hyaluronic acid modification product, in which hyaluronic acid and/or a pharmaceutically acceptable salt thereof is covalently bound to a block polymer, selected from polyethylene oxide-polypropylene oxide-polyethylene oxide block polymer, polypropylene oxide-polyethylene oxide-polypropylene oxide block polymer, polyethylene oxide-polylactic acid/polyglycolic acid copolymer-polyethylene oxide block polymer, polylactic acid/polyglycolic acid copolymer-polyethylene oxide-polylactic acid/polyglycolic acid copolymer block polymer, polyethylene oxide-polylactic acid-polyethylene oxide block polymer and polylactic acid-polyethylene oxide-polylactic acid block polymer wherein the phase transition temperature of said hyaluronic acid modification product in physiological saline and/or phosphate physiological saline is in the range from 20° C. to 35° C. when the concentration of said hyaluronic acid modification product is 10% w/v or less, wherein the most part of said block polymer is bound to said hyaluronic acid and/or a pharmaceutically acceptable salt thereof at one of the two ends of said block polymer.

2. A hyaluronic acid modification product, in which hyaluronic acid and/or a pharmaceutically acceptable salt thereof is covalently bound to a block polymer, selected from polyethylene oxide-polypropylene oxide-polyethylene oxide block polymer, polypropylene oxide-polyethylene oxide-polypropylene oxide block polymer, polyethylene oxide-polylactic acid/polyglycolic acid copolymer-polyethylene oxide block polymer, polylactic acid/polyglycolic acid copolymer-polyethylene oxide-polylactic acid/polyglycolic acid copolymer block polymer, polyethylene oxide-polylactic acid-polyethylene oxide block polymer and polylactic acid-polyethylene oxide-polylactic acid block polymer wherein the phase transition temperature of said hyaluronic acid modification product in physiological saline and/or phosphate physiological saline is in the range from 20° C. to 35° C. when the concentration of said hyaluronic acid modification product is 10% w/v or less, wherein said block polymer is bound to said hyaluronic acid and/or a pharmaceutically acceptable salt thereof at only one of the two ends of said block polymer.

3. The hyaluronic acid modification product according to claim 1, wherein said block polymer is bound to the carboxyl group of said hyaluronic acid and/or a pharmaceutically acceptable salt thereof.

4. The hyaluronic acid modification product according to claim 1, wherein the weight average molecular weight of said block polymer is 1200 daltons or more.

5. The hyaluronic acid modification product according to claim 1, wherein the ratio of introduction of said block polymer into the hyaluronic acid and/or a pharmaceutically acceptable salt thereof is at least 8 mol % per the glucuronic acid in the hyaluronic acid and/or a pharmaceutically acceptable salt thereof.

6. A hyaluronic acid modification product, in which hyaluronic acid and/or a pharmaceutically acceptable salt thereof is covalently bound to a block polymer, selected from polyethylene oxide-polypropylene oxide-polyethylene oxide block polymer, polypropylene oxide-polyethylene oxide-polypropylene oxide block polymer, polyethylene oxide-polylactic acid/polyglycolic acid copolymer-polyethylene oxide block polymer, polylactic acid/polyglycolic acid copolymer-polyethylene oxide-polylactic acid/polyglycolic acid copolymer block polymer, polyethylene oxide-polylactic acid-polyethylene oxide block polymer and polylactic acid-polyethylene oxide-polylactic acid block polymer wherein the phase transition temperature of said hyaluronic acid modification product in physiological saline and/or phosphate physiological saline is in the range from 20° C. to 35° C. when the concentration of said hyaluronic acid modification product is 10% w/v or less, wherein the weight average molecular weight of said hyaluronic acid and/or a pharmaceutically acceptable salt thereof is 1,500,000 daltons or less.

7. A pharmaceutical composition comprising the hyaluronic acid modification product according to claim 1 as an active ingredient.

8. The pharmaceutical preparation for treating joint diseases comprising the hyaluronic acid modification product according to claim 1 as an active ingredient, wherein the joint disease is loss of articular cartilage, rheumatoid arthritis, osteoarthritis or scapulo-humeral periarthritis.

9. The pharmaceutical preparation according to claim 8, which is in a form suitable to be filled in a syringe.

10. An assisting or treating agent for surgical operation, comprising the hyaluronic acid modification product according to claim 1 as its main component.

11. The assisting or treating agent according to claim 10, wherein the surgical operation is ophthalmic surgery or endoscopic mucosal resection.

12. A tissue repairing agent comprising the hyaluronic acid modification product according to claim 1 as an active ingredient.

13. The tissue repairing agent according to claim 12, which is used for repairing damage to soft tissue, atrophic irregularity after surgical operation, damage caused by Mohs' chemosurgical treatment, wrinkles or laceration scars in wrinkles.

14. The hyaluronic acid modification product according to claim 1, wherein said block polymer is a polyethylene oxide-polypropylene oxide-polyethylene oxide block polymer or a polypropylene oxide-polyethylene oxide-polypropylene oxide block polymer.

* * * * *